US012784310B2

(12) United States Patent
Bendel et al.

(10) Patent No.: US 12,784,310 B2
(45) Date of Patent: Nov. 3, 2026

(54) CONDITIONAL GENERATIVE ADVERSARIAL NETWORK (cGAN) FOR POSTERIOR SAMPLING AND RELATED METHODS

(71) Applicant: Ohio State Innovation Foundation, Columbus, OH (US)

(72) Inventors: Matthew Bendel, Columbus, OH (US); Rizwan Ahmad, Columbus, OH (US); Philip Schniter, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 263 days.

(21) Appl. No.: 18/513,006

(22) Filed: Nov. 17, 2023

(65) Prior Publication Data

US 2024/0169611 A1 May 23, 2024

Related U.S. Application Data

(60) Provisional application No. 63/426,459, filed on Nov. 18, 2022.

(51) Int. Cl.

*G06K 9/00* (2022.01)
*G06T 12/20* (2026.01)
*G16H 30/40* (2018.01)

(52) U.S. Cl.

CPC ............. *G06T 12/20* (2026.01); *G16H 30/40* (2018.01); *G06T 2211/441* (2023.08)

(58) Field of Classification Search

CPC .... G06T 12/20; G06T 2211/441; G16H 30/40
See application file for complete search history.

(56) References Cited

U.S. PATENT DOCUMENTS 10,672,153 B2 * 6/2020 Adler ...................... G06T 12/20
2018/0025271 A1 * 1/2018 Sawada .................. G06N 3/045 706/25

FOREIGN PATENT DOCUMENTS

WO WO-2021041128 A1 * 3/2021 ............... G06N 7/01

OTHER PUBLICATIONS

Adler, Jonas, and Ozan Öktem. "Deep bayesian inversion." arXiv preprint arXiv:1811.05910 (2018).
Ahmad, Rizwan, et al. "Variable density incoherent spatiotemporal acquisition (VISTA) for highly accelerated cardiac MRI." Magnetic resonance in medicine 74.5 (2015): 1266-1278.
Ajil Jalal, Marius Arvinte, Giannis Daras, Eric Price, Alex Dimakis, and Jonathan Tamir. csgm-mrilangevin. https://github.com/utcsilab/csgm-mri-langevin Accessed: Dec. 5, 2021. 6.

(Continued)

*Primary Examiner* — Xin Jia
(74) *Attorney, Agent, or Firm* — Meunier Carlin & Curfman LLC

(57) ABSTRACT

Example deep learning systems and related methods for posterior sampling in inverse problems are described herein. An example method for training a deep learning model includes receiving a training dataset including a plurality of input/output pairs; and training a conditional generative adversarial network (cGAN) using the training dataset, where the training includes a regularization process configured to enforce consistency with a posterior mean and a posterior covariance or trace-covariance.

17 Claims, 12 Drawing Sheets

400

(56) References Cited

OTHER PUBLICATIONS

Ardizzone, Lynton, et al. "Guided image generation with conditional invertible neural networks." arXiv preprint arXiv:1907.02392 (2019).
Arjovsky, Martin, Soumith Chintala, and Léon Bottou. "Wasserstein generative adversarial networks." International conference on machine learning. PMLR, 2017.
Deora, Puneesh, et al. "Structure preserving compressive sensing MRI reconstruction using generative adversarial networks." Proceedings of the IEEE/CVF Conference on Computer Vision and Pattern Recognition Workshops. 2020.
Edupuganti, Vineet, et al. "Uncertainty quantification in deep MRI reconstruction." IEEE Transactions on Medical Imaging 40.1 (2020): 239-250.
Gulrajani, Ishaan, et al. "Improved training of wasserstein gans." Advances in neural information processing systems 30 (2017).
He Sun and Katherine L Bouman. "Deep probabilistic imaging: Uncertainty quantification and multi-modal solution characterization for computational imaging." In Proc. AAAI Conf. Artificial Intell., vol. 35, pp. 2628-2637, 2021.
Heusel, Martin, et al. "Gans trained by a two time-scale update rule converge to a local nash equilibrium." Advances in neural information processing systems 30 (2017).
Isola, Phillip, et al. "Image-to-image translation with conditional adversarial networks." Proceedings of the IEEE conference on computer vision and pattern recognition. 2017.
Jalal, Ajil, et al. "Robust compressed sensing mri with deep generative priors." Advances in Neural Information Processing Systems 34 (2021): 14938-14954.
Karras, Tero, et al. "Progressive growing of gans for improved quality, stability, and variation." arXiv preprint arXiv:1710.10196 (2017).
Kingma, Diederik P., and Jimmy Ba. "Adam: A method for stochastic optimization." arXiv preprint arXiv:1412.6980 (2014).
Leone, Fred C., Lloyd S. Nelson, and R. B. Nottingham. "The folded normal distribution." Technometrics 3.4 (1961): 543-550.
Metz, Luke, et al. "Unrolled generative adversarial networks." arXiv preprint arXiv:1611.02163 (2016), 25 pages.
Ohayon, Guy, et al. "High perceptual quality image denoising with a posterior sampling cgan." Proceedings of the IEEE/cvf international conference on computer vision. 2021. 1805-1813.
Ohayon, Guy, et al. "High perceptual quality image denoising with a posterior sampling cgan." Proceedings of the ieee/cvf international conference on computer vision. 2021.
Ong, Frank, and Michael Lustig. "SigPy: a python package for high performance iterative reconstruction." Proceedings of the ISMRM 27th Annual Meeting, Montreal, Quebec, Canada. vol. 4819. No. 5. 2019.
Pruessmann, Klaas P., et al. "SENSE: sensitivity encoding for fast MRI." Magnetic Resonance in Medicine: An Official Journal of the International Society for Magnetic Resonance in Medicine 42.5 (1999): 952-962.
Radford, Alec, Luke Metz, and Soumith Chintala. "Unsupervised representation learning with deep convolutional generative adversarial networks." arXiv preprint arXiv:1511.06434 (2015).
Ronneberger, Olaf, Philipp Fischer, and Thomas Brox. "U-net: Convolutional networks for biomedical image segmentation." Medical image computing and computer-assisted intervention-MICCAI 2015: 18th international conference, Munich, Germany, Oct. 5-9, 2015, proceedings, part III 18. Springer International Publishing, 2015.
Salimans, Tim, et al. "Improved techniques for training GANs." Advances in neural information processing systems 29 (2016).
Shengyu Zhao, Jonathan Cui, Yilun Sheng, Yue Dong, Xiao Liang, Eric I Chang, and Yan Xu. Large scale image completion via co-modulated generative adversarial networks, ICLR 2021 (Spotlight). Downloaded from https: / / github.com/zsyzzsoft/comod-gan, Sep. 2022. 8.
Sohn, Kihyuk, Honglak Lee, and Xinchen Yan. "Learning structured output representation using deep conditional generative models." Advances in neural information processing systems 28 (2015).
Soloveitchik, Michael, et al. "Conditional frechet inception distance." arXiv preprint arXiv:2103.11521 (2021).
Song, Yang, and Stefano Ermon. "Improved techniques for training score-based generative models." Advances in neural information processing systems 33 (2020): 12438-12448.
Song, Yang, et al. "Solving inverse problems in medical imaging with score-based generative models." arXiv preprint arXiv:2111.08005 (2021).
Szegedy, Christian, et al. "Rethinking the inception architecture for computer vision." Proceedings of the IEEE conference on computer vision and pattern recognition. 2016.
Tonolini, Francesco, et al. "Variational inference for computational imaging inverse problems." Journal of Machine Learning Research 21.179 (2020): 1-46.
Uecker, Martin, et al. "ESPIRIT—an eigenvalue approach to autocalibrating parallel MRI: where SENSE meets GRAPPA." Magnetic resonance in medicine 71.3 (2014): 990-1001.
Wang, Zhou, et al. "Image quality assessment: from error visibility to structural similarity." IEEE transactions on image processing 13.4 (2004): 600-612.
Welling, Max, and Yee W. Teh. "Bayesian learning via stochastic gradient Langevin dynamics." Proceedings of the 28th international conference on machine learning (ICML-11). 2011, pp. 681-688.
Winkler, Christina, et al. "Learning likelihoods with conditional normalizing flows." (2019). arXiv: 1912.00042.
Yang Song, Liyue Shen, Lei Xing, and Stefano Ermon. Solving inverse problems in medical imaging with score-based generative models. Downloaded from https: / / github. com/yang-song/score_inverse_problems, Oct. 2022. 8.
Zbontar, Jure, et al. "fastMRI: An open dataset and benchmarks for accelerated MRI." arXiv preprint arXiv: 1811.08839 (2018).
Zhang, Richard, et al. "The unreasonable effectiveness of deep features as a perceptual metric." Proceedings of the IEEE conference on computer vision and pattern recognition. 2018. 586-595.
Zhang, Tao, et al. "Coil compression for accelerated imaging with Cartesian sampling." Magnetic resonance in medicine 69.2 (2013): 571-582.
Zhao, Hang, et al. "Loss functions for image restoration with neural networks." IEEE Transactions on computational imaging 3.1 (2016): 47-57.
Zhao, He, et al. "Synthesizing retinal and neuronal images with generative adversarial nets." Medical image analysis 49 (2018): 14-26.
Zhao, Shengyu, et al. "Large scale image completion via co-modulated generative adversarial networks." arXiv preprint arXiv:2103.10428 (2021).

* cited by examiner

| Model | CFID↓ | PSNR↑ | SSIM↑ | APSD | Time(4)↓ |
|---|---|---|---|---|---|
| cGAN (Adler et al.) | 36.80 | 37.31 ± 0.23 | 0.9378 ± 0.0037 | 3.7e-6 | **217 ms** |
| cGAN (Ohayon et al.) | 34.07 | 39.34* ± 0.29 | 0.9444* ± 0.0037 | 6.0e-8 | **217 ms** |
| cGAN (ours) | **22.39** | **39.36** ± 0.29 | **0.9456** ± 0.0037 | 3.7e-6 | **217 ms** |
| Langevin (Jalal et al.) | 41.03 | 37.88 ± 0.41 | 0.9042 ± 0.0062 | 5.9e-6 | 14 min |

FIG. 12

| Model | FID↓ | CFID↓ | APSD | Time(128)↓ |
|---|---|---|---|---|
| cGAN (CoModGAN) | 7.54 | 40.66 | 1.4e-2 | **144 ms** |
| cGAN (ours) | **6.45** | **39.16** | 2.1e-2 | **144 ms** |
| Langevin (Song et al.) | 18.61 | 56.92 | 2.8e-2 | 30 min |

FIG. 13

CONDITIONAL GENERATIVE ADVERSARIAL NETWORK (cGAN) FOR POSTERIOR SAMPLING AND RELATED METHODS

CROSS-REFERENCE TO RELATED APPLICATIONS

This application claims the benefit of U.S. provisional patent application No. 63/426,459, filed on Nov. 18, 2022, and titled "CONDITIONAL GENERATIVE ADVERSARIAL NETWORK (CGAN) FOR POSTERIOR SAMPLING AND RELATED METHODS," the disclosure of which is expressly incorporated herein by reference in its entirety.

GOVERNMENT SUPPORT

This invention was made with government support under EB029957 awarded by the National Institutes of Health. The government has certain rights in the invention.

BACKGROUND

In inverse problems, one seeks to reconstruct an image from incomplete and/or degraded measurements. Such problems arise in magnetic resonance imaging, computed tomography, deblurring, superresolution, inpainting, and other applications.

Image reconstruction can be used in a wide variety of applications to compensate for the limitations of imaging systems. Image reconstruction can be used to increase the resolution of an image beyond the original capture resolution ("super resolution"), inpaint missing areas of an image, reduce or eliminate errors in an image, and reduce blurring in an image.

Image reconstruction can be used for images formed based on visual light, as well as images captured using other imaging techniques like magnetic resonance imaging applications, computed tomography applications, and X-rays.

Therefore, there is a need for improved deep learning systems and related methods for posterior sampling in inverse problems, which can be applied when performing image reconstruction, for example.

SUMMARY

Deep learning systems and methods for posterior sampling in inverse problems are described herein.

In some aspects, the techniques described herein relate to a method for training a deep learning model including: receiving a training dataset including a plurality of input/output pairs; and training a conditional generative adversarial network (cGAN) using the training dataset, wherein the training includes a regularization process configured to enforce consistency with a posterior mean and a posterior variance.

In some aspects, the techniques described herein relate to a method, wherein the regularization process uses a supervised L1 loss in conjunction with a standard deviation reward.

In some aspects, the techniques described herein relate to a method, wherein the standard deviation reward is weighted.

In some aspects, the techniques described herein relate to a method, further including autotuning the standard deviation reward.

In some aspects, the techniques described herein relate to a method, wherein the trained cGAN is configured to generate a plurality of posterior input sample values for a given output value.

In some aspects, the techniques described herein relate to a method, wherein the cGAN includes a generator model and a discriminator model.

In some aspects, the techniques described herein relate to a method, wherein each of the generator model and the discriminator model includes a respective convolutional neural network (CNN).

In some aspects, the techniques described herein relate to a method, wherein the respective CNN of the generator model is configured to output images.

In some aspects, the techniques described herein relate to a method, wherein the respective CNN of the generator model is configured for image segmentation.

In some aspects, the techniques described herein relate to a method, wherein the training dataset includes images.

In some aspects, the techniques described herein relate to a method, wherein the images are medical images.

In some aspects, the techniques described herein relate to a method, wherein the medical images are magnetic resonance (MR) images.

In some aspects, the techniques described herein relate to a method, wherein the MR images are collected using Cartesian or non-Cartesian sampling masks.

In some aspects, the techniques described herein relate to a method, wherein the MR images further include a temporal dimension.

In some aspects, the techniques described herein relate to a method for posterior sampling including: providing a trained conditional generative adversarial network (cGAN), wherein a regularization process used during training of the cGAN is configured to enforce consistency with a posterior mean and a posterior variance; and generating, using the trained cGAN, a plurality of posterior input sample values for a given output value.

In some aspects, the techniques described herein relate to a method, further including training the cGAN.

In some aspects, the techniques described herein relate to a method for image reconstruction or recovery including: providing a trained conditional generative adversarial network (cGAN), wherein a regularization process used during training the cGAN is configured to enforce consistency with a posterior mean and a posterior variance; receiving a measurement from an imaging system; and generating, using the trained cGAN, a plurality of images based on the measurement.

In some aspects, the techniques described herein relate to a method, further including training the cGAN.

In some aspects, the techniques described herein relate to a system including: a conditional generative adversarial network (cGAN), wherein a regularization process used during training is configured to enforce consistency with a posterior mean and a posterior variance; a processor and a memory operably coupled to the processor, wherein the memory has computer-executable instructions stored thereon that, when executed by the processor, cause the processor to: input a measurement from an imaging system into the cGAN; and receive a plurality of images generated by the cGAN based on the measurement.

In some aspects, the techniques described herein relate to a system, wherein the cGAN is trained.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

according to implementations of the present disclosure.

Figure 9:
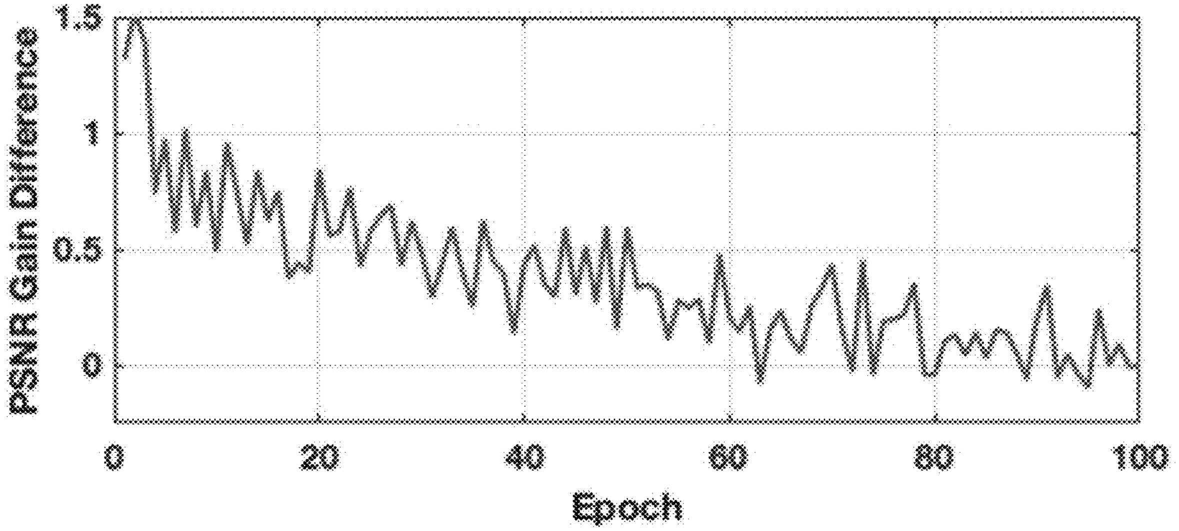

FIG. 9 illustrates a difference between P-sample PSNR gain $$\left[\frac{\hat{\varepsilon}_{P,t}}{\hat{\varepsilon}_{1,t}}\right]_{dB}$$

and theoretical value $$\left[\frac{P+1}{2P}\right]_{dB}$$

versus training epoch t for P=8, according to implementations of the present disclosure.

Figure 10:
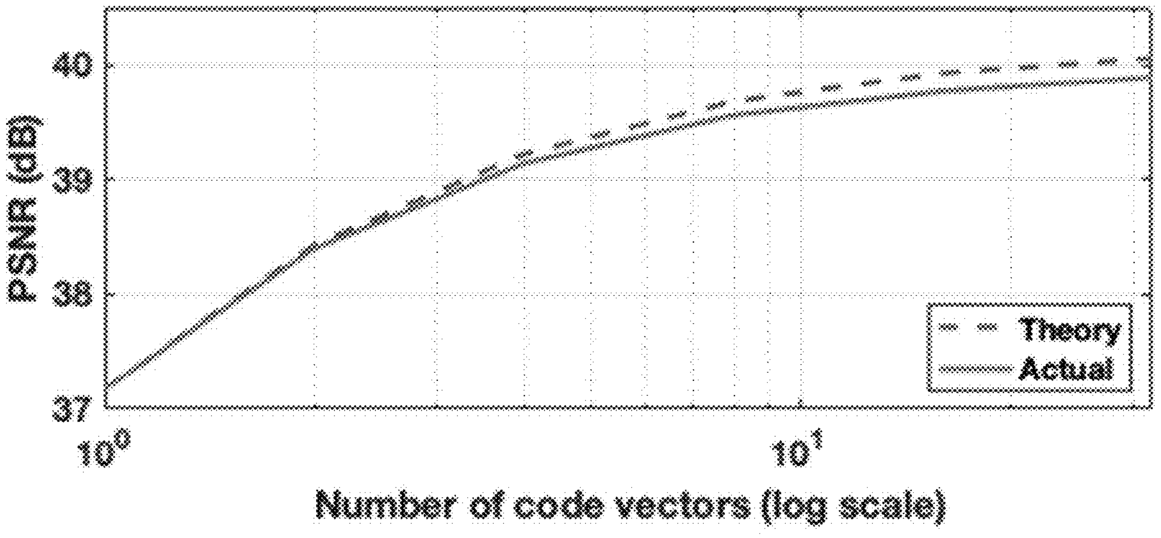

FIG. 10 illustrates PSNR of $\hat{x}_{(P)}$ versus P after autotuning and theoretical behavior when samples come from true posterior, according to implementations of the present disclosure.

Figure 11:
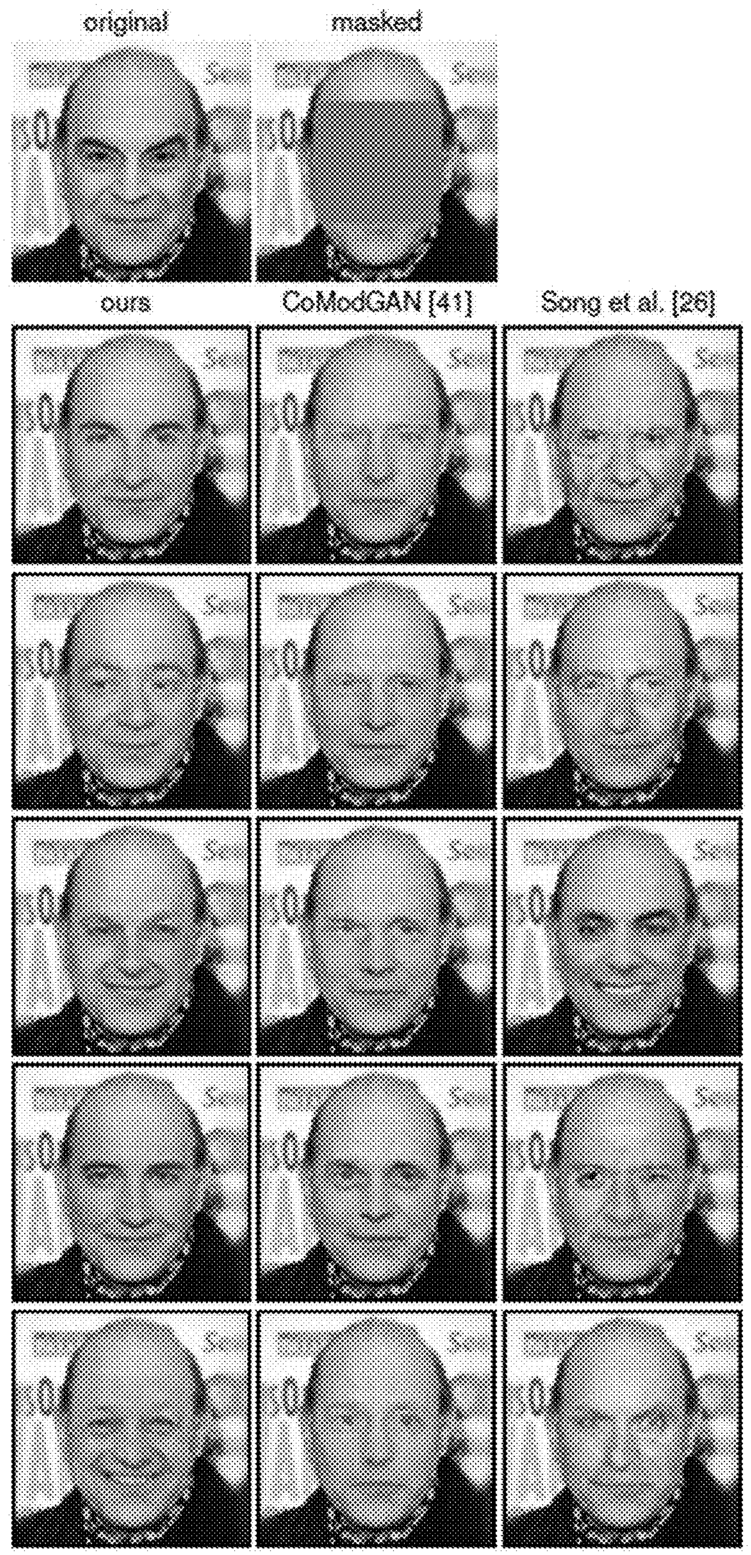

FIG. 11 illustrates an example of inpainting a 64×64 centered square on an 128×128 resolution celebA-HQ test image, according to an implementation of the present disclosure.

FIG. 12 illustrates a table of average test results for R=4 acceleration MRI reconstruction of T2 brain images at 384×384 resolution, according to implementations of the present disclosure.

FIG. 13 illustrates a table of average test results for inpainting a 64×64 centered square on 128×128 resolution celebA-HQ images, according to implementations of the present disclosure.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for reconstructing certain types of images, it will become evident to those skilled in the art that the implementations are not limited thereto, but are applicable for reconstructing any type of image.

The term "artificial intelligence" is defined herein to include any technique that enables one or more computing devices or comping systems (i.e., a machine) to mimic human intelligence. Artificial intelligence (AI) includes, but is not limited to, knowledge bases, machine learning, representation learning, and deep learning. The term "machine learning" is defined herein to be a subset of AI that enables a machine to acquire knowledge by extracting patterns from raw data. Machine learning techniques include, but are not limited to, logistic regression, support vector machines (SVMs), decision trees, Naïve Bayes classifiers, and artificial neural networks. The term "representation learning" is defined herein to be a subset of machine learning that enables a machine to automatically discover representations needed for feature detection, prediction, or classification from raw data. Representation learning techniques include, but are not limited to, autoencoders. The term "deep learning" is defined herein to be a subset of machine learning that enables a machine to automatically discover representations needed for feature detection, prediction, classification, etc. using layers of processing. Deep learning techniques include, but are not limited to, artificial neural network or multilayer perceptron (MLP).

Machine learning models include supervised, semi-supervised, and unsupervised learning models. In a supervised learning model, the model learns a function that maps an input (also known as feature or features) to an output (also known as target or targets) during training with a labeled data set (or dataset). In an unsupervised learning model, the model learns patterns (e.g., structure, distribution, etc.) within an unlabeled data set. In a semi-supervised model, the model learns a function that maps an input (also known as feature or features) to an output (also known as target or targets) during training with both labeled and unlabeled data.

Described herein are deep learning systems and related methods for posterior sampling in inverse problems. As described in the Example, the deep learning systems and related methods can be used to perform image reconstruction. Implementations of the present disclosure include improvements to training conditional generative adversarial networks (cGANs). A generative adversarial network (GAN) is an unsupervised machine learning algorithm. A GAN can include multiple (e.g., 2) neural networks competing with each other (e.g., a generator and discriminator). The generator can be a neural network trained to generate new data, and the discriminator can be trained to classify examples generated by the generator as real or fake. The two models can be trained together so that the generator model generates plausible example data. A cGAN can condition the generation of data on certain inputs to make the generated data more targeted and/or specific.

As used herein, "regularization" in machine learning refers to systems and methods of preventing overfitting of models such as the GANs and cGANs described herein. Implementations of the present disclosure can include systems and methods of regularization that use both mean values and covariance to match the "true posterior." As used herein, the "true posterior" refers to the distribution of the data in the real training data. Thus, implementations of the present disclosure can generate data with a covariance and mean similar to (or matching) the true posterior, allowing for improved generation of data in the cGAN. Thus, implementations of the present disclosure include methods for training cGAN networks, which can be used to improve the performance of those cGAN networks for image processing, as described throughout the present disclosure.

Additionally, implementations of the present disclosure include systems and methods of tuning the parameters used to train cGANs, which can optionally be used in implementations of the systems and methods for training cGANs described herein. Implementations of the present disclosure include methods of automatically tuning the βstd used to train the cGAN. As described in the Example, below, βstd can affect the variation of the samples generated in the cGAN. A common problem in the field is that existing cGANs can suffer what is referred to as "mode collapse." "Mode collapse" refers to cGANs outputting a small variety of samples, where the samples lack the variation of the true dataset. By performing automatic tuning of βstd during training, implementations of the present disclosure can train cGANs without suffering mode collapse, or with less severe mode collapse. Thus, implementations of the present disclosure include systems and methods that allow for improved training of cGAN networks to generate samples with variation that is similar to (or the same as) the variation found in the set of real training data.

Figure 1:
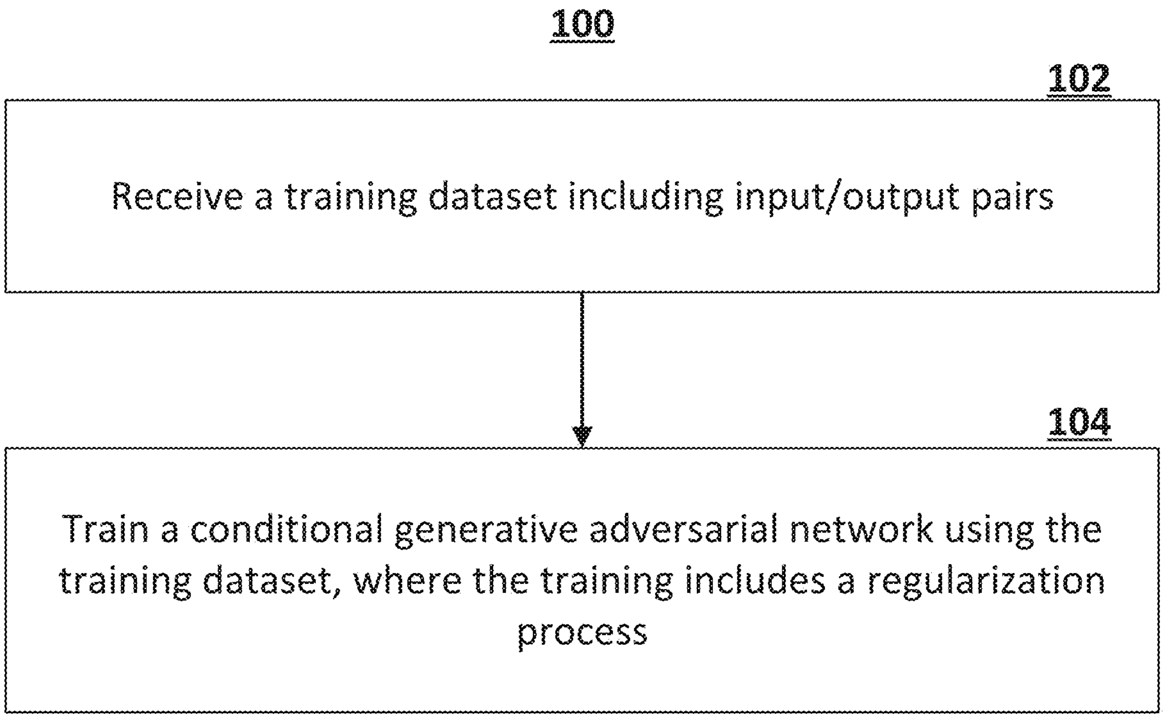
FIG. 1 illustrates a method of training a conditional generative adversarial network (cGAN), according to implementations of the present disclosure.

With reference to FIG. 1, a method 100 of training a deep learning model is illustrated. The method includes receiving a training dataset comprising a plurality of input/output pairs at step 102. As used herein, the input/output pairs received at step 102 can include any types of data. As described in the Example, the input data can include real image data, and the output data can include image data generated by a deep learning model.

The training dataset can include any type of data. As described herein, implementations of the present disclosure can be used for visual light images (e.g., photographs of people) as well as images produced using medical or scientific instruments. For example, implementations of the present disclosure can be used for computed tomography (CT) and/or magnetic resonance (MR) images. Optionally, the training dataset can be obtained from a database of medical images or photographs.

The method can further include training a conditional generative adversarial network (cGAN) using the training dataset at step 104. The training can include a regularization process configured to enforce consistency with a posterior mean and a posterior variance. As described in the Example, the regularization process used in training the cGAN can include automatically tuning βstd to prevent mode collapse. As also described in the Example, implementations of the present disclosure can further include training the cGAN so that the covariance of the generator outputs match (or is close to) the covariance of the true posterior of the training dataset used at step 104.

Different types of regularization are contemplated by the present disclosure. Optionally, the regularization process uses a supervised L1 loss in conjunction with a standard deviation reward. In some implementations, the standard deviation reward (referred to in the Example as βstd) is weighted.

In some implementations, the standard deviation reward can be autotuned.

Different configurations of cGAN are also contemplated by the present disclosure. In some implementations, the cGAN can include both a generator model and a discriminator model. The generator model and/or the discriminator model can each include a respective convolutional neural network (CNN). Optionally, the respective CNN of the generator model can be configured for image segmentation.

For example, in some implementations involving MR imaging described in the Example below, the generator model is a CNN, particularly a CNN inspired by the U-Net architecture [21] The primary input, y can be concatenated with the code vector z and fed through the U-Net. The network consists of 4 pooling layers with 128 initial channels. However, instead of pooling the study used use convolutions with filters of size 3×3, "same" padding, and a stride of 2 when downsampling. Conversely, the study upsampled using transpose convolutions, again with filters of size 3×3, "same" padding, and a stride of 2. All other convolutions utilize filters of size 3×3, "same" padding, and a stride of 1.

Within each encoder and decoder layer the example implementation included a residual block, the architecture of which can be found in [2]. The example implementation used instance-norm for all normalization layers and parametric ReLUs as our activation functions, in which the network learns the optimal "negative slope." Finally, the study included 5 residual blocks at the base of the U-Net, in between the encoder and decoder. This can be done in an effort to artificially increase the depth of the network [6]. The generator has 86,734,334 trainable parameters.

It should be understood that the generator architecture described above is only provided as an example.

Additionally, in some implementations involving MR imaging described in the Example below, the discriminator model is a CNN, particularly a CNN having 5 layers The example discriminator architecture included a discriminator that was a standard CNN with 5 layers. In the first 3 layers, the example implementation used convolutions with filter of size 4×4, "same" padding, and a stride of 2 to reduce the image resolution. The remaining two convolutional layers use the same parameters, with the stride modified to be 1. The study used batch-norm as the normalization layer and leaky ReLUs with a "negative-slope" of 0.2 as the activation functions.

The final convolutional layer does not have a normalization layer or activation function, and outputs a 1 channel "prediction map." This prediction map gives a Wasserstein score for a patch of the image. The study achieved this patch-based discrimination by utilizing the receptive field of the network used in the example implementation. Consequently, by increasing or decreasing the number of strided convolutions used in the example implementation, the study can modify the size of the patches we are discriminating. Patch-based discrimination has been known to improve the high-frequency information in reconstructions [10]. The discriminator of the example implementation has 693,057 trainable parameters.

It should be understood that the discriminator architecture described above is only provided as an example.

Further, in some implementations involving MR imaging described in the Example below, the cGANs use the generator and discriminator architectures described above. For the 3 cGANs described in the Example, the study used the architectures described herein, as well as the same, or a similar, training/testing procedure. The study adapted the model's regularization and $\beta_{adv}$ to match the authors' original implementation. In particular, when training Ohayon's cGAN we set $\beta_{adv}$=1e-3 and use $\mathcal{L}_{2,P}$ regularization while training the generator. When training Adler's cGAN, we set $\beta_{adv}$=1 and do not apply any regularization to the generator. Instead we modify the number of input channels to the discriminator and slightly modify the training logic to be consistent with the loss proposed in (7).

For Jalal's approach, the study did not modify the original implementation, other than replacing the default sampling pattern with the GRO undersampling mask. The study generated 32 samples for 72 different test images using a batch-size of 4, which took roughly 6 days. These samples were generated on a server with 4 NVIDIA V100 GPUs, each with 32 GB of memory.

It should be understood that the cGANs architecture described above is only provided as an example.

In some implementations, the trained cGAN can be configured to generate a plurality of posterior input sample values for a given output value.

Figure 2:
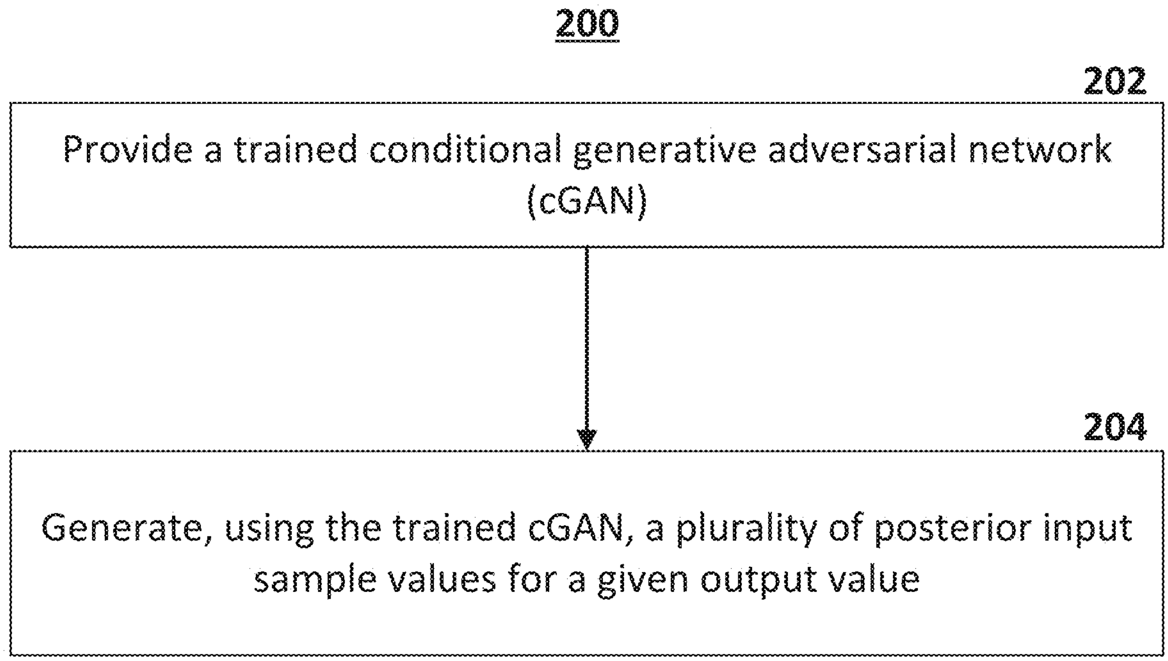
FIG. 2 illustrates a method of generating posterior input sample values using a trained cGAN, according to implementations of the present disclosure.

Implementations of the present disclosure include methods for posterior sampling. Additional description of posterior sampling is provided herein in the Example, including example implementations of posterior sampling. An example method 200 for posterior sampling is shown in FIG. 2.

The method 200 can include providing a trained conditional generative adversarial network (cGAN) at step 202, where a regularization process used during training is configured to enforce consistency with a posterior mean and a posterior variance. The trained cGAN can be trained using implementations of the method 100 described with respect to FIG. 1.

Figure 3:
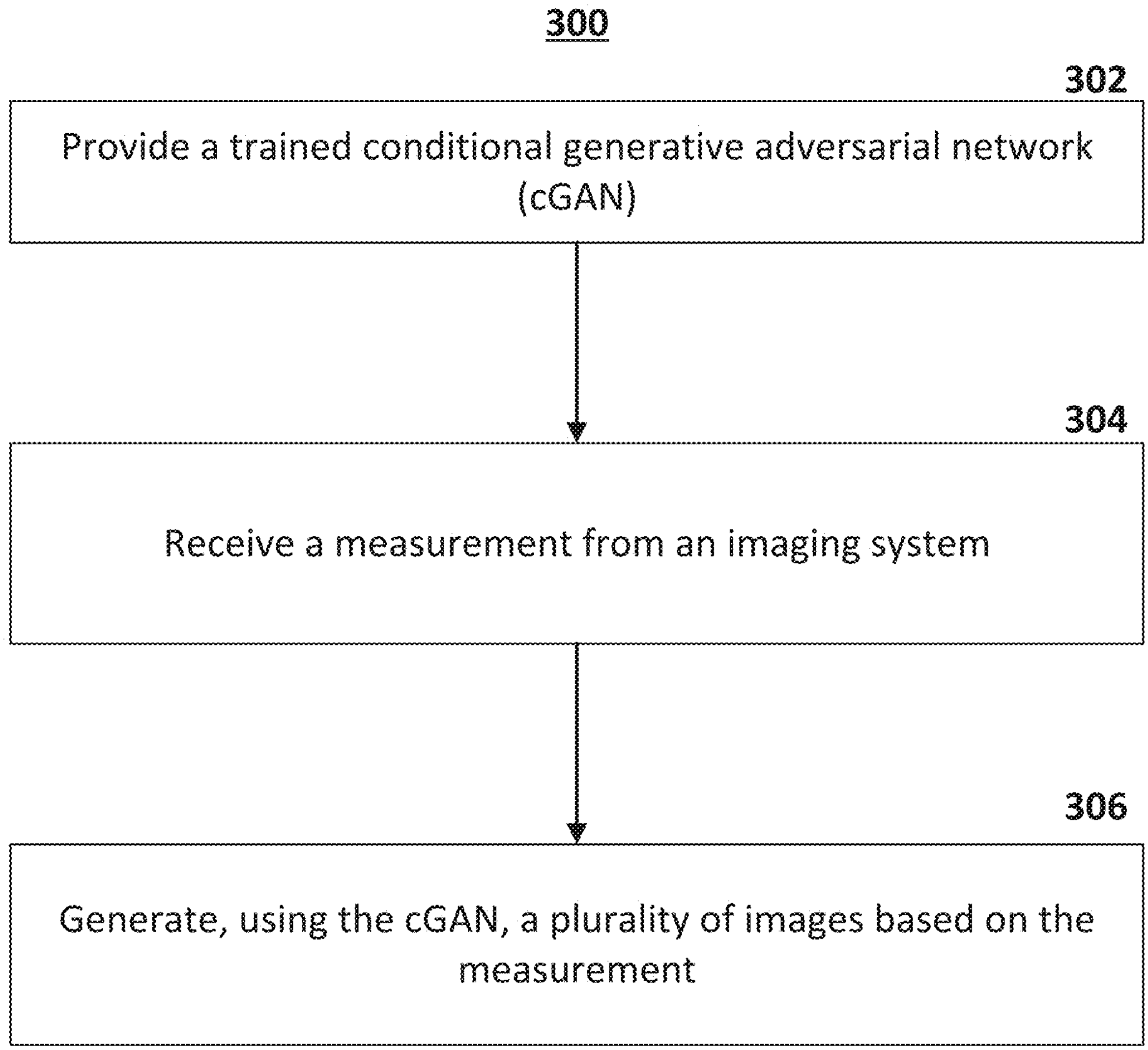
FIG. 3 illustrates a method for generating images using a trained cGAN, according to implementations of the present disclosure.

The method can further include generating, using the trained cGAN, a plurality of posterior input sample values for a given output value at step 204. Implementations of the present disclosure include methods for image reconstruction and/or recovery. An example method 300 for image reconstruction/recovery is shown in FIG. 3. The method 300 can include providing a trained conditional generative adversarial network (cGAN) at step 302. Optionally, the trained cGAN can be trained using any of the methods described with respect to FIG. 1. The regularization process used during training can be configured to enforce consistency with a posterior mean and a posterior variance.

The method 300 can further include receiving a measurement from an imaging system at step 304 and generating, using the trained cGAN, a plurality of images based on the measurement at step 306.

Figure 4:
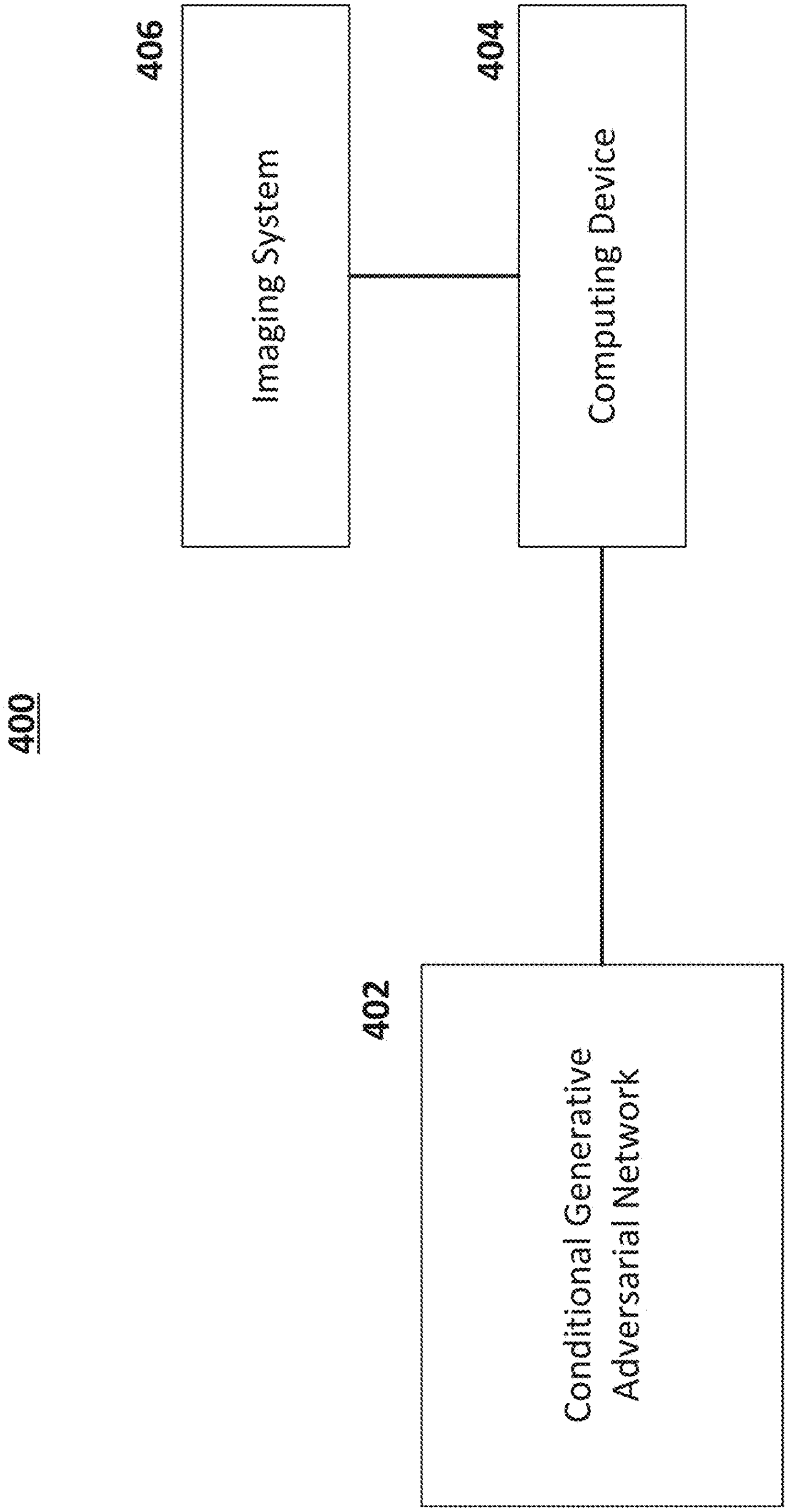
FIG. 4 illustrates a system for using a cGAN to generate images based on an input image from an imaging system, according to implementations of the present disclosure.

Implementations of the present disclosure include systems for performing image reconstruction and/or training a cGAN to perform image reconstruction. An example system 400 is shown in FIG. 4. The system 400 includes a cGAN 402, where the regularization process used during training of the cGAN 402 can be configured to enforce consistency with a posterior mean and a posterior variance. Optionally, the cGAN can be trained using any of the methods described with respect to FIG. 1.

The system 400 can also include a computing device 404. The computing device 404 can include any/all of the features of the computing device 500 shown in FIG. 5. The computing device 404 can be configured to receive input measurements from an imaging system 406, input a measurement from the imaging system 406 into the cGAN 402, and receive a plurality of images generated by the cGAN 402 based on the measurement.

The imaging system 406 can include any system that can generate any type of images. Non-limiting examples of imaging systems include MRI, CT, and imaging systems based on any wavelength of electromagnetic radiation, including visual light.

It should be appreciated that the logical operations described herein with respect to the various figures may be implemented (1) as a sequence of computer-implemented acts or program modules (i.e., software) running on a computing device (e.g., the computing device described in FIG. 5), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special-purpose digital logic, and any combination thereof. It should also be appreciated that more or fewer operations may be performed than shown in the figures and described herein. These operations may also be performed in a different order than those described herein.

Figure 5:
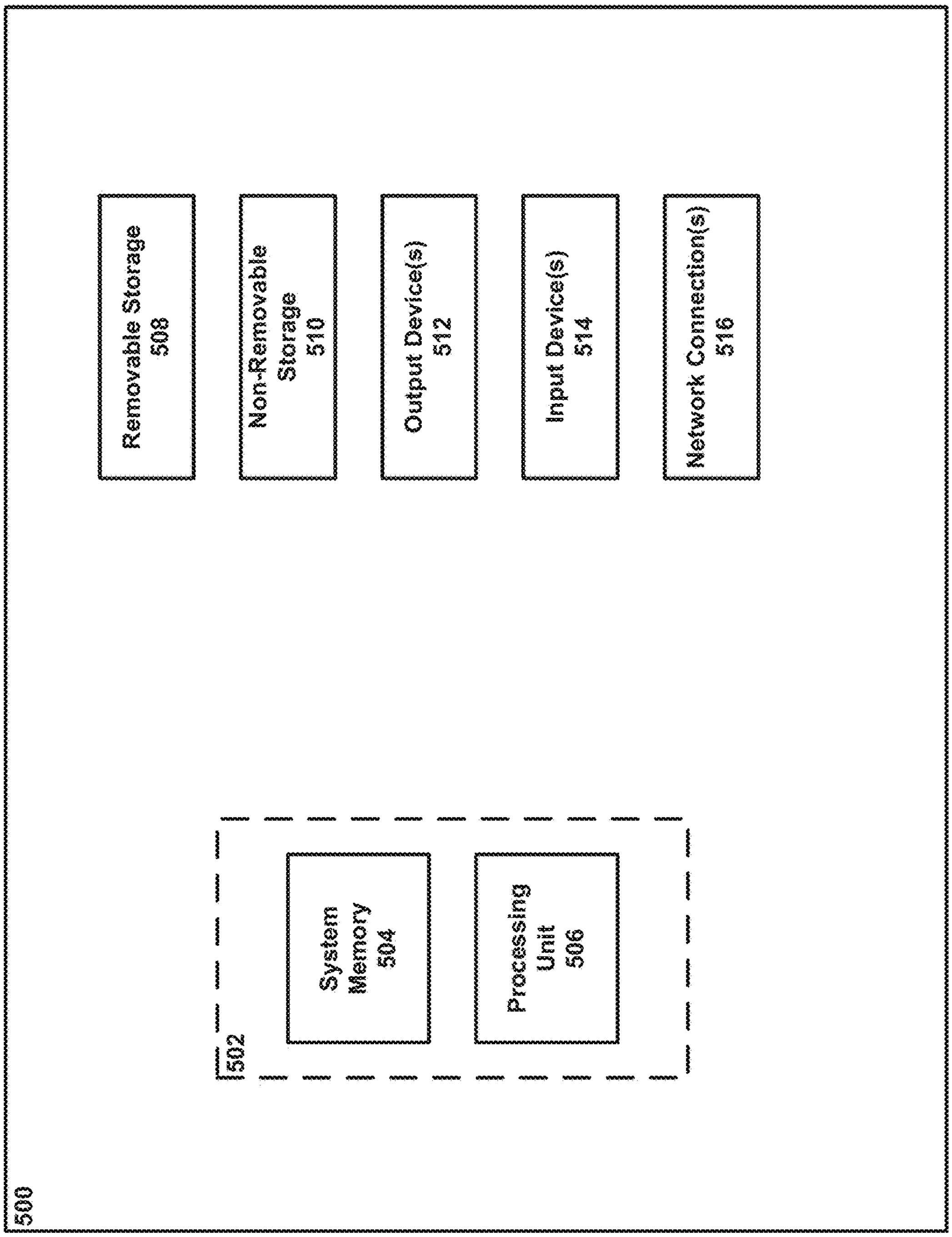
FIG. 5 is an example computing device.

Referring to FIG. 5, an example computing device 500 upon which the methods described herein may be implemented is illustrated. It should be understood that the example computing device 500 is only one example of a suitable computing environment upon which the methods described herein may be implemented. Optionally, the computing device 500 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 500 typically includes at least one processing unit 506 and system memory 504. Depending on the exact configuration and type of computing device, system memory 504 may be volatile (such as random access memory (RAM)), non-volatile (such as read-only memory (ROM), flash memory, etc.), or some combination of the two. This most basic configuration is illustrated in FIG. 4 by dashed line 502. The processing unit 506 may be a standard programmable processor that performs arithmetic and logic operations necessary for operation of the computing device 500. The computing device 500 may also include a bus or other communication mechanism for communicating information among various components of the computing device 500.

Computing device 500 may have additional features/functionality. For example, computing device 500 may include additional storage such as removable storage 508 and non-removable storage 510 including, but not limited to, magnetic or optical disks or tapes. Computing device 500 may also contain network connection(s) 516 that allow the device to communicate with other devices. Computing device 500 may also have input device(s) 514 such as a keyboard, mouse, touch screen, etc. Output device(s) 512 such as a display, speakers, printer, etc. may also be included. The additional devices may be connected to the bus in order to facilitate communication of data among the components of the computing device 500. All these devices are well-known in the art and need not be discussed at length here.

The processing unit 506 may be configured to execute program code encoded in tangible, computer-readable media. Tangible, computer-readable media refers to any media that is capable of providing data that causes the computing device 500 (i.e., a machine) to operate in a particular fashion. Various computer-readable media may be utilized to provide instructions to the processing unit 506 for execution. Example tangible, computer-readable media may include, but is not limited to, volatile media, non-volatile media, removable media and non-removable media implemented in any method or technology for storage of information such as computer-readable instructions, data structures, program modules or other data. System memory 504, removable storage 508, and non-removable storage 510 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 506 may execute program code stored in the system memory 504. For example, the bus may carry data to the system memory 504, from which the processing unit 506 receives and executes instructions. The data received by the system memory 504 may optionally be stored on the removable storage 508 or the non-removable storage 510 before or after execution by the processing unit 506.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language and it may be combined with hardware implementations.

Example

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A study was performed of an example implementation of the present disclosure can be used to reconstruct an image from incomplete and/or degraded measurements. The example implementation of the present disclosure can be used for any image reconstruction task. It should be understood that "image reconstruction," as described herein, can refer to images with any resolution, and formed using any type of imaging data. As non-limiting examples, implementations of the present disclosure can be used for magnetic resonance imaging, computed tomography, deblurring, super resolution, inpainting, and other applications using images from a wide range of imaging devices.

Implementations of the present disclosure include systems and methods that can rapidly generate high-quality posterior samples. It is often the case that many image hypotheses are consistent with both the measurements and prior information, and so implementations of the present disclosure can be configured not to recover a single "best" hypothesis but instead to sample multiple images from the posterior distribution. Implementations of the present disclosure include a regularized conditional Wasserstein GAN that can generate dozens of high-quality posterior samples per second. The study of the example implementation described herein includes quantitative evaluation metrics (e.g., conditional Frechet inception distance), showing that methods described herein produce state-of-the-art posterior samples in both parallel MRI and inpainting applications.

An example implementation includes generative posterior sampling where, given a training dataset of input/output pairs $$\{(x_t, y_t)\}_{t=1}^{T},$$

example implementations described herein can learn a generating function $\hat{x}=G_\theta(z,y)$ that, for a given y, maps random code vectors $z\sim\mathcal{N}(0,I)$ to posterior samples $\hat{x}\sim p_{x|y}(\cdot|y)$.

Posterior sampling and linear inverse problems can recover a signal or image x from a measurement y of the form $$y = Ax + w$$

where A is a known matrix and w is unknown noise. Such problems arise in deblurring, superresolution, inpainting, computed tomography (CT), magnetic resonance (MR) imaging, and other fields. When A does not have full column rank, Ax filters out any components of x that lie in the nullspace of A, and so prior information about the true x is needed for accurate recovery (e.g., the example implementation can receive information that x is an MR image, for example by tagging x, or by). But even after taking such prior information into account, there may be many hypotheses of x that yield equally good explanations of y. Thus, rather than settling for a single "best" estimate of x from y, the goal is to efficiently sample from the posterior $p_{x|y}(\cdot|y)$.

There exist several approaches that learn to sample from the posterior given training samples $$\{(x_t, y_t)\}_{t=1}^{T},$$

including conditional generative adversarial networks (cGANs) [2,10, 39], conditional variational autoencoders (cVAEs) [7,23,30], conditional normalizing flows (cNFs) [4,28,34], and scorebased generative models using Langevin dynamics [12,26, 33]. The example implementation can include cGANs, which are known to generate high-quality samples, which may be at the expense of sample diversity.

The example implementation can include a cGAN that addresses the aforementioned lack-of-diversity issue by training with a regularization that enforces consistency with the true posterior mean and covariance. The regularization can include supervised $l_1$ loss plus an appropriately weighted standard-deviation reward. In certain cases, the optimal weight can be computed in closed form. The example implementation can further include systems and methods to automatically calibrate the weight during training.

The study included accelerated MR image recovery and large-scale image completion/inpainting. To quantify performance, the study focused on conditional Frechet inception distance (CFID) [24], but the study also considers FID [9], LPIPS [36], average pixel-wise standard deviation (APSD), PSNR, and SSIM [32]. The results show the proposed regularized cGAN (rcGAN) outperforming existing cGANs [2,16] and the state-of-the-art score-based generative models from [12,26] in all tested metrics.

The example implementation can include a Wasserstein cGAN framework [2]. The Wasserstein GAN framework [5,8] can be very successful in avoiding mode collapse and stabilizing the training of GANs. The study included designing a generator network $G_\theta: \mathcal{Z}\times\mathcal{Y}\rightarrow\mathcal{X}$ such that, for typical fixed values of y, the random variable $\hat{x}=G_\theta(z,y)$ induced by $z\sim p_z$ has a distribution that best matches the posterior $p_{x|y}(\cdot|y)$ in the Wasserstein-1 distance. Here, z is drawn independently of y, and $\mathcal{X}$, $\mathcal{Y}$, and $\mathcal{Z}$ denote the spaces of signals x, measurements y, and codes z, respectively. The Wasserstein-1 distance can be expressed as [5]

$$W_1(p_{x|y}(\cdot, y), p_{\hat{x}|y}(\cdot, y)) = \sup_{D\in L_1} E_{x|y}\{D(x, y)\} - E_{\hat{x}|y}\{D(\hat{x}, y)\} \quad (2)$$

where $L_1$ denotes functions that are 1-Lipschitz with respect to their first argument and D: $\mathcal{X}\times\mathcal{Y}\rightarrow\mathbb{R}$ is a "critic" or "discriminator" that tries to distinguish between true x and generated x given y. Since the study can use a method that works for any typical value of y, the example implementation can define a loss by taking an expectation of (2) over $y\sim p_y$. As shown in [2], this expectation commutes with the supremum in (2), so that $$E_y\{W_1(p_{x|y}(\cdot, y), p_{\hat{x}|y}(\cdot, y))\} \quad (3)$$

$$= \sup_{D\in L_1} E_{x,y}\{D(x, y)\} - E_{\hat{x},y}\{D(\hat{x}, y)\}$$

$$= \sup_{D\in L_1} E_{x,z,y}\{D(x, y) - D(G_\theta(z, y), y)\} \quad (4)$$

The study optimized the generator parameters θ to minimize the loss in (4), i.e., $$\min_\theta \sup_{D\in L_1} E_{x,z,y}\{D(x, y) - D(G_\theta(z, y), y)\} \quad (5)$$

In practice, the discriminator is implemented using a neural network $D_\phi$. The parameters θ and ϕ are trained by alternately minimizing $$\mathcal{L}_{adv}(\theta, \phi) \triangleq E_{x,z,y}\{D_\phi(x, y) - D_\phi(G_\theta(z, y), y)\} \quad (6)$$

with respect to θ and minimizing $-\mathcal{L}_{adv}(\theta,\phi)+\mathcal{L}_{gp}(\phi)$ with respect to ϕ, where $\mathcal{L}_{gp}(\phi)$ is a gradient penalty that is used to encourage $D_\phi\in L_1$ [8]. In practice, the expectation over x and y in (6) can replaced by a sample average over the training examples $\{(x_t,y_t)\}$.

Mode collapse and regularization. One of the main challenges with the cGAN framework in imaging problems is that, for each training measurement example $y_t$ there is only a single signal example $x_t$. Thus, with the previously described training methodology, there may be no incentive for the generator to produce diverse samples $G(z,y_t)|_{z\sim p_z}$ for a given $y_t$. This can lead to the generator ignoring the code vector $z_t$, which is a form of "mode collapse."

With unconditional GANs (uGANs), although mode collapse was historically an issue [1,20,22], it can be largely solved by the Wasserstein GAN framework [5,8]. It should be noted that the causes of mode-collapse in uGANs are fundamentally different than in cGANs because, in the uGAN case, the training set $\{x_t\}$contains many examples of valid images, while in the cGAN case there is only one example of a valid image x, for each given measurement $y_t$. As a result, many strategies used to combat mode-collapse in uGANs are not applicable to cGANs. For example, mini-batch discrimination, where the discriminator aims to distinguish a mini-batch of true samples $\{x_t\}$ from a mini-batch of generated samples $\{x_t\}$ by leveraging inter-sample variation (e.g., MBSD [13] or its precursor from [22]), generally does not work with cGANs because the statistics of the posterior can significantly differ from the statistics of the prior.

To combat mode collapse in the cGAN case, Adler et al. [2]proposed to use a three-input discriminator $$D_\phi^{adler}: \mathcal{X}\times\mathcal{X}\times\mathcal{Y}\rightarrow\mathbb{R}$$

and replace $\mathcal{L}_{adv}$ from (6) with the loss $$\begin{aligned}\mathcal{L}_{adv}^{adler}(\theta,\phi) \triangleq E_{x,z_1,z_2,y}\Big\{\frac{1}{2}D_\phi^{adler}(x, G_\theta(z_1, y), y) \\ +\frac{1}{2}D_\phi^{adler}(G_\theta(z_2, y), x, y) \\ -D_\phi^{adler}(G_\theta(z_1, y), G_\theta(z_2, y), y)\Big\}\end{aligned} \tag{7}$$

which rewards variation between the first and second inputs of $$D_\phi^{adler}.$$

They then proved that minimizing $$\mathcal{L}_{adv}^{adler}$$

in place of $\mathcal{L}_{adv}$ does not compromise the Wasserstein cGAN objective, i.e., $$\arg\min_\theta\mathcal{L}_{adv}^{adler}(\theta,\phi)=\arg\min_\theta\mathcal{L}_{adv}(\theta,\phi).$$

Ohayon et al. [16]proposed to fight mode collapse via supervised-$l_2$ regularization [1] of $\mathcal{L}_{adv}$, i.e., $$\mathcal{L}_2(\theta) \triangleq E_{x,y}\{\|x-E_z\{G_\theta(z, y)\}\|_2^2\} \tag{8}$$

i.e., solving $\arg\min_\theta\{\mathcal{L}_{adv}(\theta,\phi)+\Delta\mathcal{L}_2(\theta)\}$ for some $\lambda>0$ when training the generator. As explained in [16], this regularization is consistent with the cGAN objective in that: if there exists some $\theta$ for which $p_{\hat{x}|y}$ matches the true posterior $p_{x|y}$ (recall that $\hat{x}\triangleq G_\theta(z,y)|_{z\sim p_z}$) then both $\mathcal{L}_{adv}$ and $\mathcal{L}_2$ are minimized by the same $\theta$. This is because $\mathcal{L}_2(\theta)$ is minimized when $E_z\{G_\theta(z,y)\}$ is the minimum mean-square error (MMSE) estimate of x from y, or equivalently the posterior mean $E_{x|y}\{x|y\}$. So, both $\mathcal{L}_{adv}$ and $\mathcal{L}_2$ are minimized by the $\theta$ for which $G_\theta$ samples from the true posterior $p_{x|y}$, if such a $\theta$ exists. In practice, such a $\theta$ may not exist, in which case $\mathcal{L}_{adv}$ and $\mathcal{L}_2$ will act in complementary ways to drive $G_\theta$ towards the true-posterior generator.

It is important to note that, in practice, the expectation $E_z$ in (8) can be replaced with a (finite) P-sample average with $P\geq 2$ (e.g., P=8 in Ohayon [17]), yielding $$\mathcal{L}_{2,P}(\theta) \triangleq = E_{x,z_1,\dots,z_P,y}\left\{\left\|x-\frac{1}{P}\sum_{i=1}^{P}G_\theta(z_i, y)\right\|_2^2\right\}$$

As shown in the study, $\mathcal{L}_{2,P}$ has the potential to induce mode collapse rather than prevent it, and the potential grows larger as P grows smaller. Supervised-$l_2$ regularization can include problems, such as mode collapse. To understand why supervised-$l_2$ regularization using a finite-sample average can lead to mode collapse, (9) can be rewritten as as $$\mathcal{L}_{2,P}(\theta) = E_y\{E_{x,z_1,\dots,z_P|y}\{\|x-\hat{x}_{(P)}\|_2^2|y\}\} \tag{10}$$

$$\begin{aligned}= E_y\Big\{\|\hat{x}_{mmse}-\overline{x}\|_2^2+\frac{1}{P}\sum_{z_i|y}\{\|d_i\|_2^2|y\} \\ +E_{x|y}\{\|e_{mmse}\|_2^2|y\}\Big\}\end{aligned} \tag{11}$$

Using:

$$\begin{aligned}&\hat{x}_i \triangleq G_\theta(z_i, y), && \hat{x}_{(P)} \triangleq \frac{1}{P}\sum_{i=1}^{P}\hat{x}_i, \\ &\overline{x} \triangleq E_{z_i|y}\{\hat{x}_i|y\}, && \overline{x} = E_{z_1,\dots,z_P|y}\{\hat{x}_{(P)}|y\}, \\ &d_i \triangleq \hat{x}_i-\overline{x}, && d_{(P)} \triangleq \frac{1}{P}\sum_{i=1}^{P}d_i, \\ &\hat{x}_{mmse} \triangleq E_{x|y}\{x|y\}, && e_{mmse} \triangleq x-\hat{x}_{mmse},\end{aligned} \tag{12}$$

noting that $E_{z_i|y}\{\hat{x}_i|y\}$ is invariant to i since $\{z_i\}$ are i.i.d.

In (11) only $\overline{x}$ and $d_i$ in (11) depend on the generator parameters $\theta$. The first term in (11) encourages $\overline{x}$ to match the MMSE estimate $\hat{x}_{mmse}$, while the second term in (11) encourages $d_i=0$ or equivalently $\hat{x}_i=\overline{x}$, which corresponds to mode collapse. Important observations are 1. As P decreases, $\mathcal{L}_{2,P}$ gives a stronger incentive to mode collapse (due to the 1/P term in (11)).
2. In the limit of $P\rightarrow\infty$, $\mathcal{L}_{2,P}$ gives no incentive to mode collapse, but also no disincentive.

Experimentally, the study observed that supervised-$l_2$ regularization does indeed lead to mode collapse when P=2. Although mode collapse may not occur with larger values of P, there is a high computational cost to using large P as a result of GPU memory constraints: as P doubles, the batch size must halve, and so training time increases linearly with P. For example, in the MRI experiment, the study found that P=2 takes approximately 2.5 days to train for 100 epochs on a 4×A100 GPU server, while P=8 takes approximately 10 days.

To mitigate $\mathcal{L}_{2,P}$'s incentive for mode-collapse, variance reward may be incorporated. In particular, training the generator can include solving:

$$\arg\min_{\theta}\{\beta_{adv}\mathcal{L}_{adv}(\theta,\phi)+\mathcal{L}_{2,var,P}(\theta,\beta_{var})\} \tag{13}$$

with some $\beta_{adv}, \beta_{var} > 0$ and $P \geq 2$ using $$\mathcal{L}_{2,var,P}(\theta,\beta_{var}) \triangleq \mathcal{L}_{2,P}(\theta)-\beta_{var}\mathcal{L}_{var,P}(\theta) \tag{14}$$

$$\mathcal{L}_{var,P}(\theta) \triangleq \frac{1}{P-1}\sum_{i=1}^{P}E_{z_1,\ldots,z_P,y}\{\|\hat{x}_i-\hat{x}_{(P)}\|_2^2\} \tag{15}$$

(15) can be rewritten as:

$$\mathcal{L}_{var,P}(\theta)=E_y\{E_{z_i|y}\{\|d_i\|_2^2 \mid y\}\} \tag{16}$$

with $d_i$ from (12), so that $$\mathcal{L}_{2,var,P}(\theta,\beta_{var}) = E_y\left\{\|\hat{x}_{mmse}-\overline{x}\|_2^2+\left(\frac{1}{P}-\beta_{var}\right)E_{z_i|y}\{\|d_i\|_2^2|y\}+E_{x|y}\{\|e_{mmse}\|_2^2|y\}\right\} \tag{17}$$

(17) shows that minimizing the regularization $\mathcal{L}_{2,var,P}(\theta,\beta_{var})$ with $\beta_{var}=1/P$ encourages $\overline{x}$ to match the MMSE estimate $\hat{x}_{mmse}$ without encouraging or discouraging mode collapse. To discourage mode collapse, using $\beta_{var}>1/P$ may be used, but in this case $\mathcal{L}_{2,var,P}(\theta,\beta_{var})$ would encourage the norm of $d_i$ (i.e., trace covariance of $\hat{x}_i$) to be as large as possible, which is not the aim of the example implementation. Instead, the study configures a regularizer that encourages the covariance of $\hat{x}_i$ to match the true posterior covariance, but it is not clear that this can be accomplished using $\mathcal{L}_{2,P}$-based regularization.

The study included quantifying performance using CFID.

As described herein, the study included training a generator $G_\theta$ so that, for typical fixed values of y, the distribution $p_{\hat{x}|y}$ matches the true posterior $\beta_{x|y}(\cdot|y)$. It is essential to have a quantitative metric for evaluating performance with respect to this goal. For example, it is not enough that the generated samples are "accurate" in the sense that $\hat{x}_i$ or $\hat{x}_{(P)}$ are close to the ground truth x, nor is it enough that $\hat{x}_i$ are "diverse" in the sense of having a large element-wise standard deviation.

Thus, the study quantified the performance of posterior approximation using the conditional Frechet inception distance (CFID) [24], which is a computationally efficient approximation to the conditional Wasserstein distance (CWD)

$$CWD \triangleq E_y\{W_2(p_{x|y}(\cdot,y),p_{\hat{x}|y}(\cdot,y))\} \tag{18}$$

In (18), $W_2(p_a,p_b)$ denotes the Wasserstein-2 distance between distributions $p_a$ and $p_b$, defined as $$W_2(p_a,p_b) \triangleq \min_{p_{a,b}\in\Pi(p_a,p_b)} E_{a,b}\{\|a-b\|_2^2\} \tag{19}$$

$$\Pi(p_a,p_b) \triangleq \left\{p_{a,b}: p_a=\int p_{a,b}\,db \text{ and } p_b=\int p_{a,b}\,da\right\}$$

where $\Pi(p_a, p_b)$ denotes the set of joint distributions $p_{a,b}$ with prescribed marginals $p_a$ and $p_b$. Similar to how the Frechet inception distance (FID) [9]—a method used to evaluate unconditional GAN peformance-is computed, CFID approximates CWD (18) as follows: i) the random vectors x and $\hat{x}$ are replaced by low-dimensional embeddings $\underline{x}$ and $\underline{\hat{x}}$, typically generated using the Inception v3 network [29], and ii) the embedding distributions $p_{\underline{x}|y}$ and $p_{\underline{\hat{x}}|y}$ are approximated by Gaussians $\mathcal{N}(\mu_{x|y},\Sigma_{xx|y})$ and $\mathcal{N}(\mu_{\underline{\hat{x}}|y},\Sigma_{\underline{\hat{x}}|y})$. With these approximations, the CWD reduces to $$CIFD \triangleq E_y\|\mu_{x|y}-\mu_{\underline{x|y}}\|_2^2 - +tr\left[\sum_{\underline{xx|y}}+\sum_{\underline{x|y}}-2\left(\sum_{\underline{xx|y}}^{1/2}\sum_{\underline{x|y}}\sum_{\underline{xx|y}}^{1/2}\right)\right]\Big\}. \tag{20}$$

In practice, the expectations, means, and covariances in (20) are replaced by sample averages using samples $\{(x_t,y_t)\}$ from a test set.

The example implementation includes systems and methods for Regularization using supervised-$l_1$ plus standarddeviation reward.

Unlike the previously described forms of regularization, implementations of the present disclosure include forms of cGAN regularization that encourage the samples $\hat{x}_i$ to match the true posterior in both mean and covariance. As a non-limiting example, when training the generator, the example implementation can solve:

$$\arg\min_{\theta}\{\beta_{adv}\mathcal{L}_{adv}(\theta,\phi)+\mathcal{L}_{1,std,P}(\theta,\beta_{std})\} \tag{21}$$

with some $\beta_{adv},\beta_{std}>0$ and $P\geq 2$, where regularizer $$\mathcal{L}_{1,std,P}(\theta,\beta_{std}) \triangleq \mathcal{L}_{1,P}(\theta)-\beta_{std}L_{std,P}(\theta) \tag{22}$$

is constructed from P-sample supervised-$l_1$ loss and standard-deviation reward:

$$\mathcal{L}_{1,P}(\theta) \triangleq E_{x,z_1,\ldots,z_P,y}\{\|x-\hat{x}_{(P)}\|_1\} \tag{23}$$

$$L_{std,P}(\theta) \triangleq \sqrt{\frac{\pi}{2P(P-1)}}\sum_{i=1}^{P}E_{z_1,\ldots,z_P,y}\{\|\hat{x}_i-\hat{x}_{(P)}\|_1\} \tag{24}$$

where $\hat{x}_i$ and $\hat{x}_{(P)}$ were defined in (12).

Figure 6A:
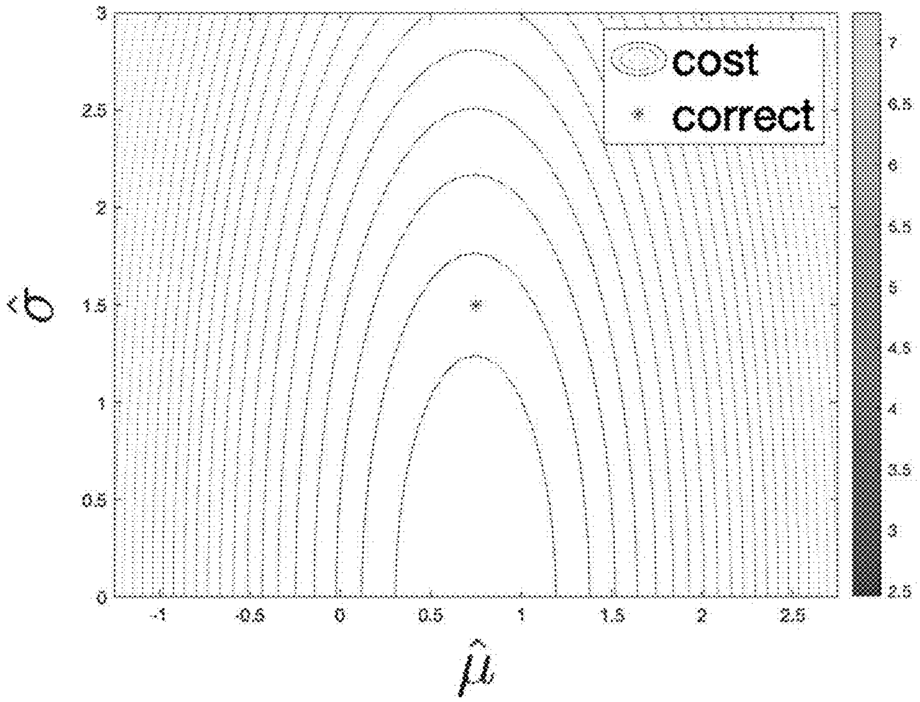
FIG. 6A illustrates an example Scalar-Gaussian illustration of a supervised-L2 regularizer at P=8.
Figure 6B:
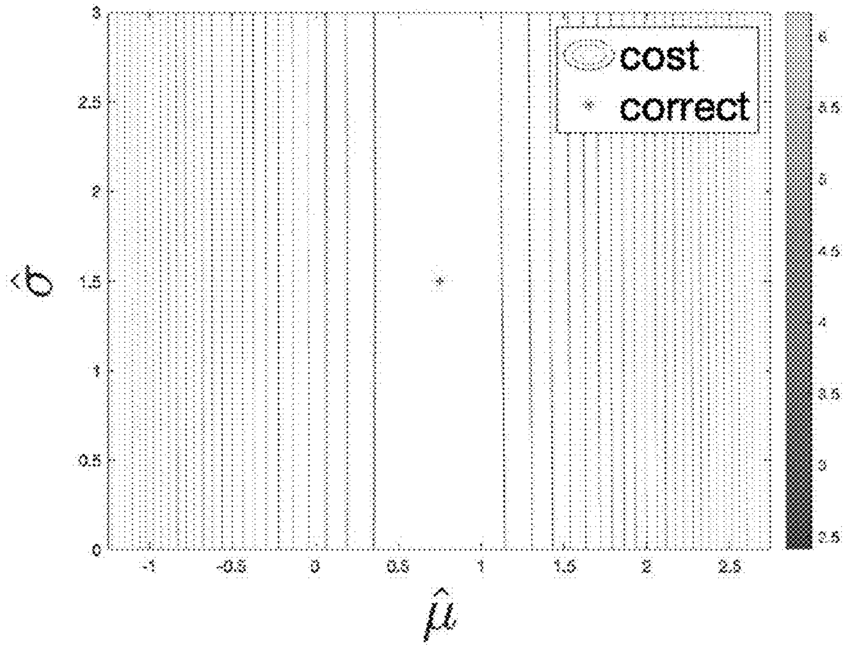
FIG. 6B illustrates an example Scalar-Gaussian illustration of a supervised-L2 plus variance reward regularizer with $\beta_{var}$=1/P at P=8.
Figure 6C:
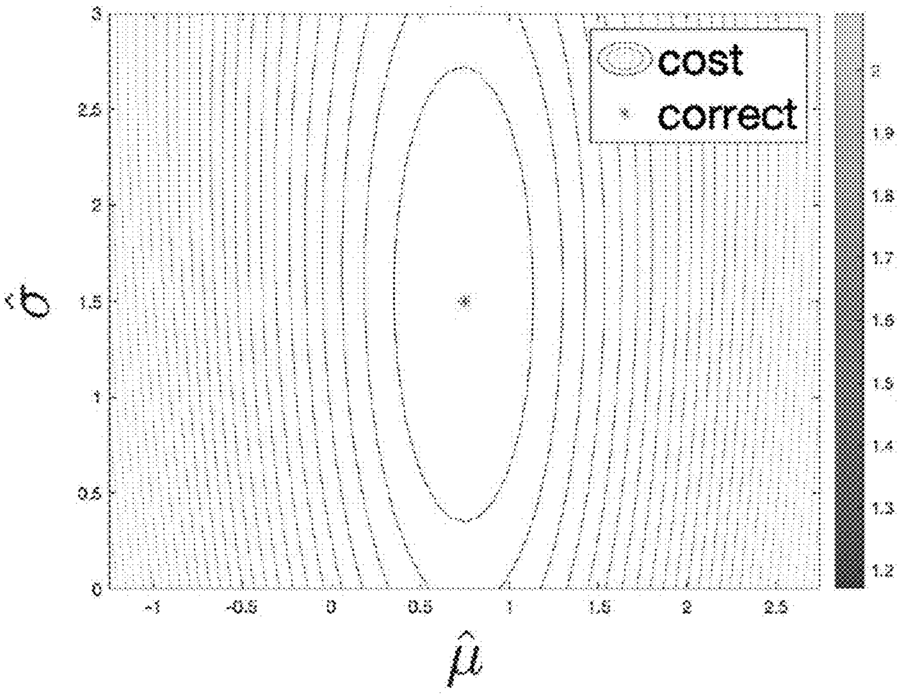
FIG. 6C illustrates an example Scalar-Gaussian illustration of a supervised-L1 plus std reward regularizer with $$\beta_{std} = \beta_{std}^{N} \text{ at } P = 8.$$

The study found that P=2 worked best for an example implementation, as shown in FIGS. 6A-6C. From a computational perspective, this is highly advantageous because, as discussed earlier, the time to train the network increases linearly with P.

For image recovery in general, the use of supervised-$l_1$ loss is often preferred over $l_2$ because it results in sharper, more visually pleasing results [38]. But regularizing a cGAN using supervised-$l_1$ loss alone can push the generator towards mode collapse, for reasons similar to the supervised-$l_2$ case.

Implementations of the present disclosure can use a properly weighted standard deviation (std) reward in conjunction with supervised $l_1$ loss, as in (22). The study shows that the std reward works together with the $l_1$ loss to enforce the correctness of both the posterior mean and the posterior covariance. This stands in contrast to the case of $l_2$ loss with a variance reward, which enforces only the correctness of the posterior mean.

Proposition 1. Assume that P≥2 and that θ has complete control over the y-conditional mean and covariance of $\hat{x}_i$. Then the regularization-minimizing parameters $$\theta_* = \text{argmin}_\theta \mathcal{L}_{1,std,,}(\theta, \beta^N_{std}) \text{ with}$$

$$\beta^N_{std} \triangleq \sqrt{\frac{2}{\pi P(P+1)}} \tag{25}$$

yield generated statistics $$E_{z_i|y}\{\hat{x}_i(\theta_*)|y\} = E_{x|y}\{x \mid y\} = \hat{x}_{mmse} \tag{26a}$$

$$Cov_{z_i|y}\{\hat{x}_i(\theta_*)|y\} = Cov_{x|y}\{x \mid y\} \tag{26b}$$

when the elements of $\hat{x}_i$ and x are independent Gaussian conditioned on y. Thus, the $\mathcal{L}_{1,\ std,P}$ regularization encourages the y-conditional mean and covariance of $\hat{x}_i$ to match those of the true x.

In practical applications, $\hat{x}_i$ and x are not expected to be independent Gaussian conditioned on y, as assumed in Proposition 1. So, using $$\mathscr{B}^N_{std}$$

from (25) may not work well in practice. Implementations of the present disclosure include methods to automatically determine the correct $\beta_{std}$ To illustrate the behavior of the previously described regularizers, the study considered the scalar-Gaussian case, where the generator is $G_\theta(z,y)=\hat{\mu}+\hat{\sigma}z$, with code $z\sim\mathcal{N}(0,1)$ and parameters $\theta=[\hat{\mu},\hat{\sigma}]^T$. In this case, the generated posterior is $p_{\hat{x}|y}(x|y)=\mathcal{N}(x;\hat{\mu},\hat{\sigma}^2)$, and the study assumes that the true posterior is $p_{x|y}(x|y)=\mathcal{N}(x;\mu,\sigma^2)$ for some μ and σ>0.

Figure 6D:
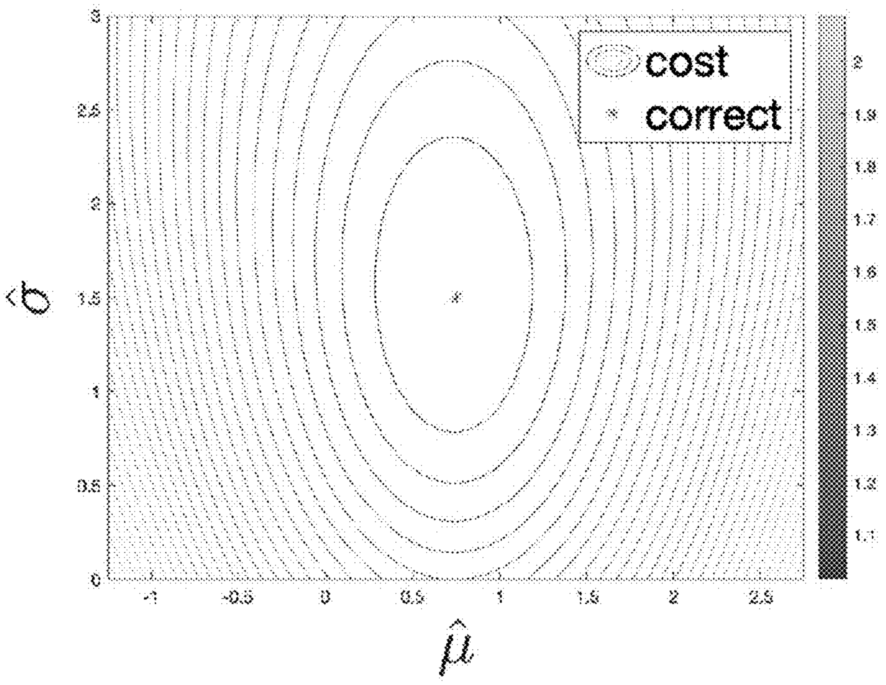
FIG. 6D illustrates an example Scalar-Gaussian illustration of supervised-L1 plus std reward regularizer with $$\beta_{std} = \beta_{std}^{N} \text{ at } P = 2$$

FIG. 6A plots P-sample supervised-L2 loss $\mathcal{L}_{2,P}(\theta)$ from (9) versus θ for P=8. The plot shows that the minimizing $\theta_*=\arg\min_\theta \mathcal{L}_{2,P}(\theta)$ yields $\hat{\mu}=\mu$ and $\hat{\sigma}=0$, which corresponds to mode collapse. FIG. 6B plots P-sample supervised-L2 loss plus variance reward $\mathcal{L}_{2,\ var,P}(\theta,\beta_{var})$ from (14) versus θ for $\beta_{var}=1/P$ and P=8. This choice of $\beta_{var}$ cancels the middle term in (11), which is responsible for mode collapse. As can be seen in FIG. 6B, $\theta_*=\arg\min_0 \mathcal{L}_{2,\ var,P}(\theta,\beta_{var})$ is no longer unique, and there is no incentive for mode collapse (i.e., $\hat{\sigma}=0$) but no incentive to match the true posterior (i.e., $\hat{\sigma}=\sigma$). FIG. 6C plots P-sample supervised-L1 loss plus std reward $\mathcal{L}_{1,\ std,P}(\theta,\beta_{std})$ versus θ from (22) for $$\beta_{std} = \beta^N_{std}$$

from (25) and P=8. The plots shows that $\theta_*=\arg\min_\theta \mathcal{L}_{1,std,P}(\theta,\beta_{std})$ recovers the true parameters (i.e., $\theta_*=[\mu,\sigma]^T$) as predicted by Proposition 1. Finally, FIG. 6D repeats the experiment from FIG. 6C, but with P=2. The plot shows $\theta_*=[\mu,\sigma]^T$ as predicted by Proposition 1. But, comparing FIG. 6D to FIG. 6C, the cost surface becomes steeper for smaller P, i.e., the regularization becomes stronger. In real-world experiments, the study finds that some example implementations of $\mathcal{L}_{1,std,P}(\theta,\beta_{std})$-regularized cGANs work best when trained with the minimum value of P=2.

Implementations of the present disclosure include systems and methods of autotuning $\beta_{std}$.

The example implementation includes methods to autotune $\beta_{std}$ for a given training dataset. The example approach can be based on the principle that larger values of $\beta_{std}$ tend to yield samples $\hat{x}_i$ with more variation. But more variation is not necessarily better; implementations of the present disclosure can generate samples with the correct amount of variation. To assess variation, the study can compare the expected $l_2$ error of the P-sample average $\hat{x}_{(P)}$ to that of $\hat{x}_{(1)}$). In the case of mode collapse, these errors are identical. But when $\{\hat{x}_i\}$ are true posterior samples, these errors follow a particular relationship:

Given generator outputs $\{\hat{x}_i\}$ and their P sample average $$\hat{x}_{(P)} \triangleq \frac{1}{P}\sum_{i=1}^{P}\hat{x}_i,$$

the study defined the expected $l_2$ error on $\hat{x}_{(p)}$ as $$\mathcal{E}_P \triangleq E\{\|\hat{x}_{(P)} - x\|_2^2|y\}$$

If $\{\hat{x}_i\}$ are independent samples of the true posterior (i.e., $\hat{x}_i\sim p_{x|y}(\cdot|y)$), then $$\varepsilon_P = \frac{P+1}{P}\varepsilon_{mmse} \text{ and so } \frac{\varepsilon_P}{\varepsilon_1} = \frac{P+1}{2P} \tag{28}$$

Figure 7:
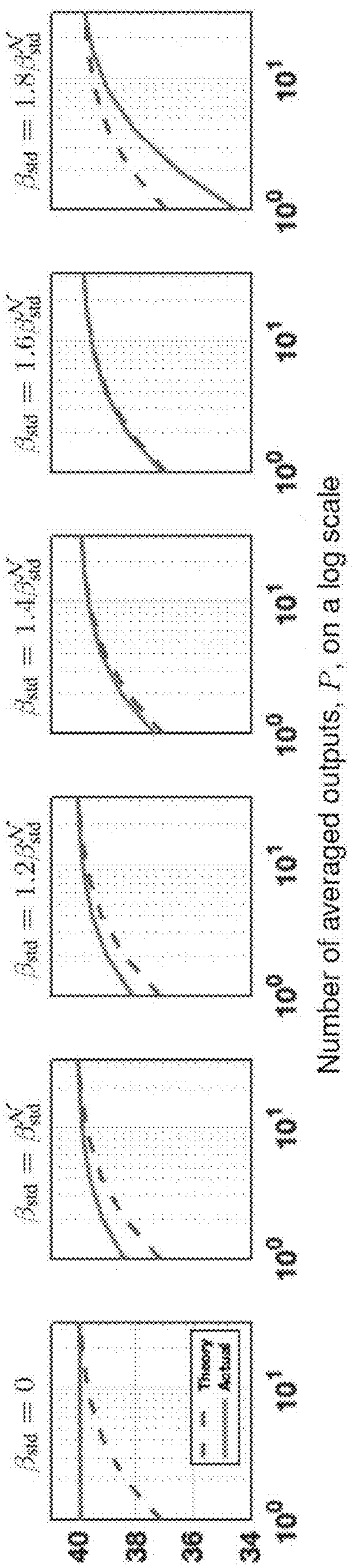
FIG. 7 illustrates example PSNR of $\hat{x}_{(P)}$ versus P, the number of averaged outputs, for several values of βstd used during training as well as the theoretical behavior for true-posterior samples.

FIG. 7 shows that, for any P≥2, $\varepsilon_P/\varepsilon_1$ grows with $\beta_{std}$. Together, Proposition 2 and FIG. 7 can suggest to adjust $\beta_{std}$ so that $\varepsilon_P/\varepsilon_1$ ratio obeys (28). In practice, at each epoch t, the study can approximate $\varepsilon_P$ and $\varepsilon_1$ using a validation pair $(x_t,y_t)$ as follows:

$$\hat{\varepsilon}_{P,t} \triangleq \left\|\frac{1}{P}\sum_{i=1}^{P}G_\theta(z_{i,t},y_t) - x_t\right\|_2^2$$

$$\hat{\varepsilon}_{1,t} \triangleq \|G_\theta(z_{1,t},y_t) - x_t\|_2^2,$$

where i.i.d. codes $$\{z_{i,t}\}_{i=1}^{P}$$

are drawn independently of $x_t$ and $y_t$. The example implementation can update $\beta_{std}$ using gradient descent:

$$\beta_{std,t+1} = \beta_{std,r} - \mu_{std}\left(\left[\frac{P+1}{2P}\right]_{dB} - \left[\frac{\hat{\varepsilon}_{P,t}}{\hat{\varepsilon}_{1,t}}\right]_{dB}\right)\beta^N_{std} \tag{31}$$

with $$\beta_{std,0} = \beta^N_{std}, \text{ some } \mu_{std} > 0, \text{ and } [x]_{dB} \triangleq 10\log_{10}(x).$$

Implementations of the present disclosure can include systems and methods to enforce data consistency.

The example data-consistency procedures described herein can be optionally used with implementations of the cGAN described herein. In some applications such as medical imaging or inpainting, the end user may feel comfortable knowing that all generated reconstructions $\hat{x}_i$ of x from y=Ax+w (recall (1)) are consistent with the measurements in that $$y = A\hat{x}_i \tag{32}$$

The example recovery method aims to restore the information about x that was lost through the measurement process (i.e., the components of x lying in the nullspace of A) and so this approach applies when A has a non-trivial nullspace. Also, if no attempt is made to remove the noise w in y, the approach may be appropriate only for high-SNR applications.

The proposed data-consistency approach leverages the fact that, if (32) holds, then $A^+y=A^+A\hat{x}_i$ must also hold, where $(\bullet)^+$ denotes the pseudo-inverse. The quantity $A^+A$ can be recognized as the orthogonal projection matrix associated with the row space of A. So, (32) says that the components of $\hat{x}_i$ in the row space of A must equal $A^+y$ while the components in the null space are unconstrained.

This implies the following data-consistency procedure:

$$\hat{x}_i = (I - A^+A)\hat{x}_i^{raw} + A^+y. \tag{33}$$

where $$\hat{x}_i^{raw}$$

is the raw generator output, $\hat{x}_i$ is the the data consistent output, and $I-A^+A$ is the orthogonal projection matrix associated with the null space of A.

The study of the example implementation further included MRI experiments using implementations of the present disclosure.

In the MRI version of (1), x is a complex-valued multicoil image. For the training $\{x_t\}$, the study used the top 8 slices of all fastMRI [35]T2 brain training volumes with at least 16 coils, cropping them to 384×384 pixels and compressing to 8 virtual coils [37], yielding 12200 training images. Then 2376 testing and 784 validation images were obtained in the same manner from the fastMRI T2 brain testing volumes. From the 2376 testing images, the study randomly selected 72 from which to compute performance metrics, in order to limit the evaluation time of the Langevin competitor [12] to roughly 6 days. To create measurement data $y_t$, the study transformed $x_t$ to the Fourier domain, sampled using the GRO pattern [3] at acceleration R=4, and transformed the zero-filled k-space measurements back to the (complex, multicoil) image domain.

The study architecture used a U-Net [21] for the generator and a standard CNN for the discriminator. The discriminator was patch-based [10]since that gave slightly improved performance. Also, the study used the data-consistency processing from Section 3.3.

At each training iteration, the generator takes in $n_{batch}$ measurement samples $y_t$, and P code vectors for every $y_t$, and performs an optimization step on the loss $$\mathcal{L}_G(\theta) \triangleq \beta_{adv}\mathcal{L}_{adv}(\theta, \phi) + L_{1,P}(\theta) - \beta_{std}\mathcal{L}_{std,P}(\theta)$$

where by default the study used $\beta_{adv}$=1e-2, $n_{batch}$=40, P=2, and updated $\beta_{std}$ according to (31). The discriminator then takes in the $Pn_{batch}$ generator outputs and performs an optimization step on the loss $$\mathcal{L}_D(\phi) = -\mathcal{L}_{adv}(\theta, \phi) + \alpha_1\mathcal{L}_{gp}(\phi) + \alpha_2 L_{drift}(\phi),$$

where $\mathcal{L}_{gp}$ is the gradient penalty from [8], $\mathcal{L}_{drift}$ is the drift penalty from [13], and $\alpha_1$=10 and $\alpha_2$=0.001 from [13]. The study used one discriminator update per generator update [13]. The models were trained for 100 epochs using the Adam optimizer [14] with a learning rate of 1e-3, $\beta_1$=0, and $\beta_2$=0.99, as in [13]. Running PyTorch on a server with 4 Tesla A100 GPUs, each with 82 GB of memory, the training of an MRI cGAN took approximately 2.5 days.

The study included validation and testing of the example implementations described herein. To evaluate performance, the study converted the multi-coil generator outputs to complex-valued images using SENSE-based coil combining [19] with ESPIRiTestimated [31] coil sensitivity maps (via SigPy [18]). The study then converted to the magnitude domain before computing CFID, PSNR, SSIM, and average pixel-wise standard deviation (APSD), defined as $$\left(\frac{1}{NP}\sum_{i=1}^{P}\|\hat{x}_{(P)} - \hat{x}_i\|^2\right)^{1/2}.$$

PSNR and SSIM were computed from the P-averaged outputs $\hat{x}_{(P)}$ (recall (12)), while CFID was computed from the un-averaged outputs $\hat{x}_i$. The study used P=32 for testing and P=8 for validation.

The study compared the example implementation of a cGAN according to the present disclosure to Adler et al.'s cGAN [2], Ohayon et al.'s cGAN [16], and the fastMRI Langevin approach from Jalal et al. [12]. The cGAN from [2] uses generator loss $\beta_{adv}$ $\mathcal{L}_{adv}(\theta,\phi)$ and discriminator loss $$-\mathcal{L}_{adv}^{adler}(\theta, \phi) + \alpha_1\mathcal{L}_{gp}(\phi) + \alpha_2 L_{drift}(\phi),$$

while the cGAN from [16] uses generator loss $\gamma_{adv}$ $\mathcal{L}_{adv}(\theta,\phi)+\mathcal{L}_{2,P}(\theta)$ and discriminator loss $-\mathcal{L}_{adv}(\theta,\phi)+\alpha_1\mathcal{L}_{gp}+\alpha_2\mathcal{L}_{drift}(\phi)$, where for each the study used the value of $\beta_{adv}$ from the original paper. All cGANs used the same generator and discriminator architectures, except that [2] used extra discriminator input channels to facilitate the 3-input loss (7). For the Langevin approach [12], the study did not modify the implementation from [11] except for the undersampling mask.

For the MRI experiment described herein, the test CFID, PSNR, SSIM, APSD, and evaluation time (for 4 samples) are shown in FIG. 12. The values shown represent an average over the 72 test samples, with standard error shown after the \pm. FIG. 12 shows that the implementation of the present disclosure yielded significantly better CFID than the competitors. The implementation of the present disclosure also yielded the highest PSNR and SSIM, although they were both within one standard error of the values from Ohayon et al.'s cGAN. Ohayon et al.'s APSD was almost two orders of magnitude lower than those from the other approaches, indicating mode collapse. The cGANs generated samples 3800 times faster than the Langevin approach.

Figure 8:
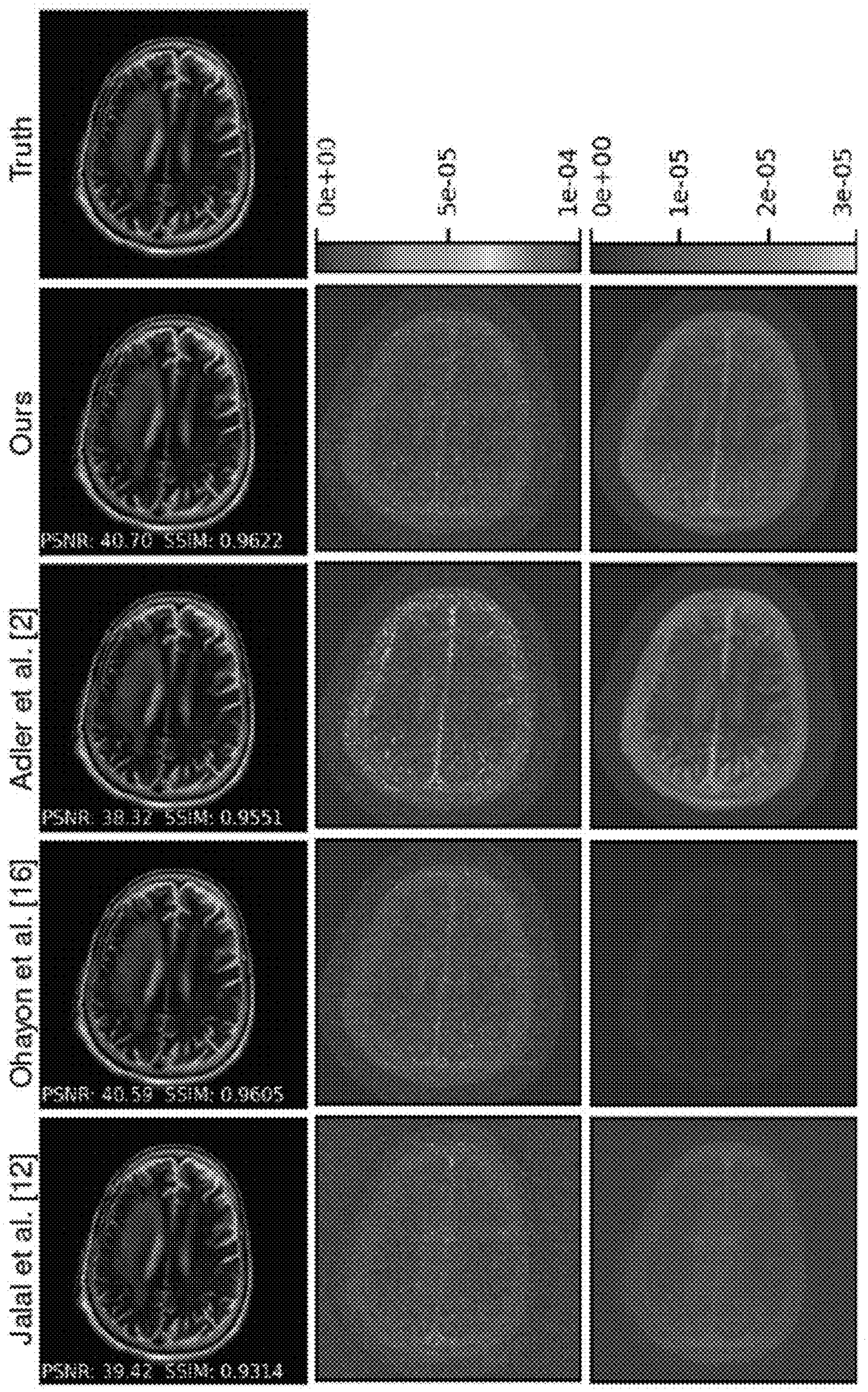
FIG. 8 illustrates an example of MRI reconstruction of a test image including reconstruction $\hat{x}_{(P)}$, pixel-wise absolute error $|\hat{x}_{(P)}-x|$, and pixel-wise standard-deviation $$\left(\frac{1}{P}\sum_{i=1}^{P}(\hat{x}_i - \hat{x}_{(P)})^2\right)^{1/2},$$

FIG. 8 shows example test-image reconstructions for the four different methods under test, along with the corresponding pixel-wise absolute errors $|\hat{x}_{(P)}-x|$ and pixel-wise standard deviations $$\left(\frac{1}{P}\sum_{i=1}^{P}(\|\hat{x}_{(P)}-\hat{x}_i\|)^2\right)^{1/2}.$$

The mode collapse of Ohayon et al.'s cGAN is evident from the dark pixel-wise standard deviation image. The fact that the cGAN errors are less than the Langevin errors near the image corners is a consequence of minor differences in sensitivity-map estimation relative to [11].

$\beta_{std}$ autotuning results. FIG. 9 shows the difference between the P-sample PSNR gain $$\left[\frac{\hat{\varepsilon}_{P,t}}{\hat{\varepsilon}_{1,t}}\right]_{dB}$$

and the theoretical value $$\left[\frac{P+1}{2P}\right]_{dB}$$

versus the training epoch t for P=8, as used during validation. As described herein the observed P-sample PSNR gain $$\left[\frac{\hat{\varepsilon}_{P,t}}{\hat{\varepsilon}_{1,t}}\right]_{dB}$$

is dependent on $\beta_{std}$, which is adapted according to (31). FIG. 10 shows the PSNR of test $\hat{x}_{(p)}$ versus P after autotuning. The figure shows that the observed curve closely matches the theoretical curve corresponding to true-posterior samples.

The study further included inpainting experiments using an example implementation of the present disclosure. The study objective was to complete the missing centered 64×64 square of an 128×128 CelebA-HQ face image [13]. The study randomly split the dataset, yielding 27000 images for training, 2000 for validation, and 1000 for testing. This application is qualitatively different from MR image recovery in that the study man not aim to recover the ground-truth image but rather hallucinate faces that are consistent with the unmasked pixels.

For the inpainting experiments, the architecture in the study included the CoModGAN architecture from [41] along with the proposed $\mathcal{L}_{1,\ std,P}$ regularization, but the study did not use MBSD [13] at the discriminator, as in the original CoModGAN.

The study further included training, validation and testing of an example implementation of the present disclosure configured for inpainting. The study used the same general training and testing procedure described previously with respect to the study, but with $\beta_{adv}$=5e-3, $n_{batch}$=128, and 110 epochs of cGAN training. Also, the study computed FID and LPIPS instead of PSNR and SSIM, since the goal of the inpainting experiment was not to recover the original image but rather generate faces with high perceptual quality and diversity. Running PyTorch on a server with 4 Tesla A100 GPUs, each with 82 GB of memory, the cGAN training took approximately 1.5 days.

The study compared an example implementation of the present disclosure with CoModGAN [41] with truncation parameter $\psi$=1, as well as the Langevin approach from Song et al. [25]. For CoModGAN, the study used the implementation [40]. For Song et al., the study used the authors' implementation from [27] after training their NCSNv2 model on the 128×128 celebA-HQ dataset using their celeba.yml configuration.

Reconstruction results from the study were recorded. FIG. 13 shows the average test FID, CFID, APSD, and evaluation time (for 128 samples). It shows that the example implementation yielded a small but noticeable improvement over CoModGAN, and a large improvement over the Langevin method, in both FID and CFID. All approaches gave roughly similar APSD, but the cGANs generated samples 12500 times faster than the Langevin approach.

FIG. 11 shows five image samples for the three methods under test. The samples show that the samples generated by the example implementation have higher quality than those of Song et al. and more variation than those of CoModGAN.

Implementations of the present disclosure include regularization techniques for cGANs including supervised-$l_1$ loss plus an appropriately weighted standard-deviation reward, i.e., $\mathcal{L}_{1,P}(\theta)$-$\beta_{std}$ $\mathcal{L}_{std,P}(\theta)$. The study shows that, for an independent Gaussian posterior, with appropriate $\beta_{std}$, minimizing the regularization yields generator samples that agree with the true posterior samples in both mean and covariance. Implementations of the present disclosure further include methods to autotune $\beta_{std}$, which can be used with practical data.

For example implementations including multicoil MR reconstruction and large-scale image inpainting, the study showed that the example implementations (with appropriate choice of generator and discriminator architecture) can outperform state-of-the-art cGAN and Langevin competitors in CFID as well as accuracy metrics like PSNR and SSIM (for MRI) and perceptual metrics like FID (for inpainting). Compared to Langevin approaches, the method produces samples thousands of times faster.

It should be understood that the study and example implementations described with respect to the study are intended only as non-limiting examples. For example, the example implementations of the present disclosure include a cGAN is trained for a specific A from (1), however, it should be understood that additional types of A matrices can be used, and that the A matrix described herein is only a non-limiting example. In the inpainting and MR applications, for example, the generator could take in both the measurements y and the sampling mask. It should also be understood that the applications of the example implementation described in the study are also intended only as non-limiting examples. Additional non-limiting example applications of implementations of the present disclosure include any imaging application, including computed tomography (CT), superresolution, and/or deblurring.

REFERENCES

[1] Unrolled generative adversarial networks. In Proc. Int. Conf. on Learn. Rep., 2016. 2

[2] Jonas Adler and Ozan Öktem. Deep Bayesian inversion. arXiv: 1811.05910,2018.1,2,6,7,17,18,19,20

[3] Rizwan Ahmad, Hui Xue, Shivraman Giri, Yu Ding, Jason Craft, and Orlando P. Simonetti. Variable density incoherent spatiotemporal acquisition (VISTA) for highly accelerated cardiac mri. Magn. Reson. Med., 74, 2015.6

[4] Lynton Ardizzone, Carsten Lüth, Jakob Kruse, Carsten Rother, and Ullrich Köthe. Guided image generation with conditional invertible neural networks. arXiv: 1907.02392, 2019. 1

[5] Martin Arjovsky, Soumith Chintala, and Léon Bottou. Wasserstein generative adversarial networks. In Proc. Int. Conf. Mach. Learn., volume 70, pages 214-223, Aug. 2017. 1,2

[6] Puneesh Deora, Bhavya Vasudeva, Saumik Bhattacharya, and Pyari Mohan Pradhan. Structure preserving compressive sensing MRI reconstruction using generative adversarial networks. In Proc. IEEE Conf. Comp. Vision Pattern Recog. Workshop, pages 22112219, June 2020. 17

[7] Vineet Edupuganti, Morteza Mardani, Shreyas Vasanawala, and John Pauly. Uncertainty quantification in deep MRI reconstruction. IEEE Trans. Med. Imag., 40(1): 239-250, Jan. 2021. 1

[8] Ishaan Gulrajani, Faruk Ahmed, Martin Arjovsky, Vincent Dumoulin, and Aaron Courville. Improved training of Wasserstein GANs. In Proc. Neural Inf. Process. Syst. Conf., page 5769-5779, 2017. 1, 2, 6

[9] Martin Heusel, Hubert Ramsauer, Thomas Unterthiner, Bernhard Nessler, and Sepp Hochreiter. GANs trained by a two time-scale update rule converge to a lo cal Nash equilibrium. In Proc. Neural Inf. Process. Syst. Conf., volume 30, 2017. 1, 3

[10] Phillip Isola, Jun-Yan Zhu, Tinghui Zhou, and Alexei A Efros. Image-to-image translation with conditional adversarial networks. In Proc. IEEE Conf. Comp. Vision Pattern Recog., pages 1125-1134, 2017. 1, 2, 4, 6, 17

[11] Ajil Jalal, Marius Arvinte, Giannis Daras, Eric Price, Alex Dimakis, and Jonathan Tamir. csgm-mrilangevin. https://github/com/utcsilab/csgm-mri-langevin. Accessed: 2021-12-05. 6

[12] Ajil Jalal, Marius Arvinte, Giannis Daras, Eric Price, Alex Dimakis, and Jonathan Tamir. Robust compressed sensing MRI with deep generative priors. In Proc. Neural Inf. Process. Syst. Conf., 2021. 1, 6, 7, 18, 19, 20

[13] Tero Karras, Timo Aila, Samuli Laine, and Jaakko Lehtinen. Progressive growing of GANs for improved quality, stability, and variation. In Proc. Int. Conf. on Learn. Rep., 2018. 2, 6, 7

[14] Diederik P. Kingma and Jimmy Ba. Adam: A method for stochastic optimization. In Proc. Int. Conf. on Learn. Rep., 2015. 6

[15] Fred C Leone, Lloyd S Nelson, and RB Nottingham. The folded normal distribution. Technometrics, 3(4):543-550, 1961. 12, 13

[16] Guy Ohayon, Theo Adrai, Gregory Vaksman, Michael Elad, and Peyman Milanfar. High perceptual quality image denoising with a posterior sampling CGAN. In Proc. IEEE Int. Conf. Comput. Vis. Workshops, volume 10, pages 1805-1813, 2021. 1, 2, 6, 7, 18, 19, 20

[17] Guy Ohayon, Theo Adrai, Gregory Vaksman, Michael Elad, and Peyman Milanfar. High perceptual quality image denoising with a posterior sampling cgan. Downloaded from https://github.com/theoad/pscgan, Jul. 2021. 2

[18] Frank Ong and Michael Lustig. SigPy: A python package for high performance iterative reconstruction. In Proc. Annu. Meeting ISMRM, volume 4819, 2019. 6

[19] Klaas P. Pruessmann, Markus Weiger, Markus B. Scheidegger, and Peter Boesiger. SENSE: Sensitivity encoding for fast MRI. Magn. Reson. Med., 42(5):952-962, 1999. 6, 16

[20] Alec Radford, Luke Metz, and Soumith Chintala. Unsupervised representation learning with deep convolutional generative adversarial networks. arXiv: 1511.06434, 2015. 2

[21] Olaf Ronneberger, Philipp Fischer, and Thomas Brox. U-Net: Convolutional networks for biomedical image segmentation. In Proc. Intl. Conf. Med. Image Comput. Comput. Assist. Intervent., pages 234-241, 2015. 6, 17

[22] Tim Salimans, Ian Goodfellow, Wojciech Zaremba, Vicki Cheung, Alec Radford, and Xi Chen. Improved techniques for training GANS. In Proc. Neural Inf. Process. Syst. Conf., volume 29, 2016. 2

[23] Kihyuk Sohn, Honglak Lee, and Xinchen Yan. Learning structured output representation using deep conditional generative models. In Proc. Neural Inf. Process. Syst. Conf., 2015. 1

[24] Michael Soloveitchik, Tzvi Diskin, Efrat Morin, and Ami Wiesel. Conditional Frechet inception distance. arXiv:2103.11521, 2021. 1, 3, 14

[25] Yang Song and Stefano Ermon. Improved techniques for training score-based generative models. In Proc. Neural Inf. Process. Syst. Conf., 2020. 8 [26] Yang Song, Liyue Shen, Lei Xing, and Stefano Ermon. Solving inverse problems in medical imaging with score-based generative models. In Proc. Int. Conf. on Learn. Rep., 2022. 1, 8, 21, 22, 23, 24

[27] Yang Song, Liyue Shen, Lei Xing, and Stefano Ermon. Solving inverse problems in medical imaging with score-based generative models. Downloaded from https://github.com/yang-song/score_inverse_problems, Oct. 2022. 8

[28] He Sun and Katherine L Bouman. Deep probabilistic imaging: Uncertainty quantification and multi-modal solution characterization for computational imaging. In Proc. AAAI Conf. Artificial Intell., volume 35, pages 2628-2637, 2021. 1

[29] Christian Szegedy, Vincent Vanhoucke, Sergey loffe, Jon Shlens, and Zbigniew Wojna. Rethinking the inception architecture for computer vision. In Proc. IEEE Conf. Comp. Vision Pattern Recog., 2016. 3

[30] Francesco Tonolini, Jack Radford, Alex Turpin, Daniele Faccio, and Roderick Murray-Smith. Variational inference for computational imaging inverse problems. J. Mach. Learn. Res., 21(179):1-46, 2020. 1

[31] Martin Uecker, Peng Lai, Mark J Murphy, Patrick Virtue, Michael Elad, John M Pauly, Shreyas S Vasanawala, and Michael Lustig. ESPIRiT-an eigenvalue approach to autocalibrating parallel MRI: Where SENSE meets GRAPPA. Magn. Reson. Med., 71(3):990-1001, 2014. 6, 16

[32] Zhou Wang, Alan C Bovik, Hamid R Sheikh, and Eero P Simoncelli. Image quality assessment: From error visibility to structural similarity. IEEE Trans. Image Process., 13(4):600-612, Apr. 2004. 1

[33] Max Welling and Yee W Teh. Bayesian learning via stochastic gradient Langevin dynamics. In Proc. Int. Conf. Mach. Learn., pages 681-688, 2011. 1

[34] Christina Winkler, Daniel Worrall, Emiel Hoogeboom, and Max Welling. Learning likelihoods with conditional normalizing flows. arXiv preprint arXiv:1912.00042, 2019. 1

[35] Jure Zbontar, Florian Knoll, Anuroop Sriram, Matthew J. Muckley, Mary Bruno, Aaron Defazio, Marc Parente, Krzysztof J. Geras, Joe Katsnelson, Hersh Chandarana, Zizhao Zhang, Michal Drozdzal, Adriana Romero, Michael Rabbat, Pascal Vincent, James Pinkerton, Duo Wang, Nafissa Yakubova, Erich Owens, C. Lawrence Zitnick, Michael P. Recht, Daniel K. Sodickson, and Yvonne W. Lui. fastMRI: An open dataset and benchmarks for accelerated MRI. arXiv:1811.08839, 2018. 6, 16 [36] Richard Zhang, Phillip Isola, Alexei A Efros, Eli Shechtman, and Oliver Wang. The unreasonable effectiveness of deep features as a perceptual metric. In Proc. IEEE Conf. Comp. Vision Pattern Recog., pages 586-595, 2018. 1

[37] Tao Zhang, John M Pauly, Shreyas S Vasanawala, and Michael Lustig. Coil compression for accelerated imaging with Cartesian sampling. Magn. Reson. Med., 69(2):571-582, 2013. 6

[38] Hang Zhao, Orazio Gallo, luri Frosio, and Jan Kautz. Loss functions for image restoration with neural networks. IEEE Trans. Comput. Imag., 3(1):47-57, Mar. 2017. 4

[39] He Zhao, Huiqi Li, Sebastian Maurer-Stroh, and Li Cheng. Synthesizing retinal and neuronal images with generative adversarial nets. Med. Image Analysis, 49, 07 2018. 1, 4

[40] Shengyu Zhao, Jonathan Cui, Yilun Sheng, Yue Dong, Xiao Liang, Eric I Chang, and Yan Xu. Large scale image completion via co-modulated generative adversarial networks, ICLR 2021 (Spotlight). Downloaded from https://github.com/zsyzzsoft/comod-gan, Sep. 2022. 8

[41] Shengyu Zhao, Jonathan Cui, Yilun Sheng, Yue Dong, Xiao Liang, Eric I-Chao Chang, and Yan Xu. Large scale image completion via co-modulated generative adversarial networks. In Proc. Int. Conf. on Learn. Rep., 2021. 7, 8, 21, 22, 23, 24

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for training a deep learning model comprising:

receiving a training dataset comprising a plurality of input/output pairs; and training a conditional generative adversarial network (cGAN) using the training dataset, wherein the training comprises a regularization process configured to enforce consistency with a posterior mean and a posterior covariance or trace-covariance, wherein the regularization process uses a supervised L1 loss in conjunction with a standard deviation reward, the standard deviation reward being weighted by a standard deviation reward weight (βstd), and wherein training further comprises autotuning βstd by:

(a) selecting a validation input/output pair;

(b) for an output value of the validation input/output pair, generating, using the cGAN, P samples corresponding to the output value using P independently drawn random code vectors, where P is an integer greater than 1;

(c) computing a P-sample average of the P samples;

(d) computing (i) a first squared L2 error between the P-sample average and a ground-truth input value of the validation input/output pair and (ii) a second squared L2 error between one of the P samples and the ground-truth input value;

(e) computing a ratio of the first squared L2 error to the second squared L2 error; and (f) updating βstd using gradient descent to reduce a difference between the ratio and (P+1)/(2P).

2. The method of claim 1, wherein, during the training of the cGAN, for a same output value of an input/output pair, the cGAN generates two samples using two independently drawn random code vectors, and the supervised L1 loss is computed between a ground-truth input value of the input/output pair and an average of the two samples.

3. The method of claim 2, wherein the standard deviation reward is based on a sum of L1-norm deviations of the two samples from the average of the two samples, and wherein the regularization process subtracts βstd times the standard deviation reward from the supervised L1 loss.

4. The method of claim 3, wherein the autotuning of βstd is performed at each training epoch using a validation input/output pair for the training epoch, and wherein the P independently drawn random code vectors are drawn independently of the validation input/output pair.

5. The method of claim 1, wherein the trained cGAN is configured to generate a plurality of posterior input sample values for a given output value.

6. The method of claim 1, wherein the cGAN comprises a generator model and a discriminator model.

7. The method of claim 6, wherein each of the generator model and the discriminator model comprises a respective convolutional neural network (CNN).

8. The method of claim 7, wherein the respective CNN of the generator model is configured to output images.

9. The method of claim 8, wherein the respective CNN of the generator model is configured for image segmentation.

10. The method of claim 1, wherein the training dataset comprises images.

11. The method of claim 10, wherein the images are medical images.

12. The method of claim 11, wherein the medical images are magnetic resonance (MR) images.

13. The method of claim 12, wherein the MR images are collected using Cartesian or non-Cartesian sampling masks.

14. The method of claim 12, wherein the MR images further include a temporal dimension.

15. A method for posterior sampling comprising:

providing a trained conditional generative adversarial network (cGAN), wherein a regularization process used during training of the cGAN is configured to enforce consistency with a posterior mean and a posterior covariance or trace-covariance; and generating, using the trained cGAN, a plurality of posterior input sample values for a given output value, wherein the cGAN is trained by:

receiving a training dataset comprising a plurality of input/output pairs; and training a conditional generative adversarial network (cGAN) using the training dataset, wherein the training comprises a regularization process configured to enforce consistency with a posterior mean and a posterior covariance or trace-covariance, wherein the regularization process uses a supervised L1 loss in conjunction with a standard deviation reward, the standard deviation reward being weighted by a standard deviation reward weight (βstd), and wherein training further comprises autotuning βstd by:

(a) selecting a validation input/output pair;

(b) for an output value of the validation input/output pair, generating, using the cGAN, P samples corresponding to the output value using P independently drawn random code vectors, where P is an integer greater than 1;

(c) computing a P-sample average of the P samples;

(d) computing (i) a first squared L2 error between the P-sample average and a ground-truth input value of the validation input/output pair and (ii) a second squared L2 error between one of the P samples and the ground-truth input value;

(e) computing a ratio of the first squared L2 error to the second squared L2 error; and (f) updating βstd using gradient descent to reduce a difference between the ratio and (P+1)/(2P).

16. A method for image reconstruction or recovery comprising: providing a trained conditional generative adversarial network (cGAN), wherein a regularization process used during training of the cGAN is configured to enforce consistency with a posterior mean and a posterior covariance or trace-covariance;

receiving a measurement from an imaging system; and generating, using the trained cGAN, a plurality of images based on the measurement, wherein the cGAN is trained by:

receiving a training dataset comprising a plurality of input/output pairs; and training a conditional generative adversarial network (cGAN) using the training dataset, wherein the training comprises a regularization process configured to enforce consistency with a posterior mean and a posterior covariance or trace-covariance, wherein the regularization process uses a supervised L1 loss in conjunction with a standard deviation reward, the standard deviation reward being weighted by a standard deviation reward weight (βstd), and wherein training further comprises autotuning βstd by:

(a) selecting a validation input/output pair;

(b) for an output value of the validation input/output pair, generating, using the cGAN, P samples corresponding to the output value using P independently drawn random code vectors, where P is an integer greater than 1;

(c) computing a P-sample average of the P samples;

(d) computing (i) a first squared L2 error between the P-sample average and a ground-truth input value of the validation input/output pair and (ii) a second squared L2 error between one of the P samples and the ground-truth input value;

(e) computing a ratio of the first squared L2 error to the second squared L2 error; and (f) updating βstd using gradient descent to reduce a difference between the ratio and (P+1)/(2P).

17. A system comprising:

a conditional generative adversarial network (cGAN), wherein a regularization process used during training is configured to enforce consistency with a posterior mean and a posterior covariance or trace-covariance; a processor and a memory operably coupled to the processor, wherein the memory has computer-executable instructions stored thereon that, when executed by the processor, cause the processor to: input a measurement from an imaging system into the cGAN; and receive a plurality of images generated by the cGAN based on the measurement, wherein the cGAN is trained by:

receiving a training dataset comprising a plurality of input/output pairs; and training a conditional generative adversarial network (cGAN) using the training dataset, wherein the training comprises a regularization process configured to enforce consistency with a posterior mean and a posterior covariance or trace-covariance, wherein the regularization process uses a supervised L1 loss in conjunction with a standard deviation reward, the standard deviation reward being weighted by a standard deviation reward weight (βstd), and wherein training further comprises autotuning βstd by:

(a) selecting a validation input/output pair;

(b) for an output value of the validation input/output pair, generating, using the cGAN, P samples corresponding to the output value using P independently drawn random code vectors, where P is an integer greater than 1;

(c) computing a P-sample average of the P samples;

(d) computing (i) a first squared L2 error between the P-sample average and a ground-truth input value of the validation input/output pair and (ii) a second squared L2 error between one of the P samples and the ground-truth input value;

(e) computing a ratio of the first squared L2 error to the second squared L2 error; and (f) updating βstd using gradient descent to reduce a difference between the ratio and (P+1)/(2P).

* * * * *